United States Patent
Sato et al.

(10) Patent No.: US 10,777,751 B2
(45) Date of Patent: Sep. 15, 2020

(54) TRUXENE DERIVATIVE AND ORGANIC ELECTROLUMINESCENCE DEVICE INCLUDING THE SAME

(71) Applicant: SAMSUNG DISPLAY CO., LTD., Yongin-si, Gyeonggi-do (KR)

(72) Inventors: Shuri Sato, Yokohama (JP); Shigeyuki Yagi, Osaka (JP)

(73) Assignee: Samsung Display Co., Ltd., Yongin-si (KR)

( * ) Notice: Subject to any disclaimer, the term of this patent is extended or adjusted under 35 U.S.C. 154(b) by 28 days.

(21) Appl. No.: 15/242,022

(22) Filed: Aug. 19, 2016

(65) Prior Publication Data
US 2017/0054080 A1    Feb. 23, 2017

(30) Foreign Application Priority Data

Aug. 21, 2015  (JP) .................................. 2015-164108
May 10, 2016  (JP) .................................. 2016-094230

(51) Int. Cl.
| H01L 51/00 | (2006.01) |
| C07D 307/91 | (2006.01) |
| C07D 209/86 | (2006.01) |
| C07D 333/76 | (2006.01) |
| C09K 11/02 | (2006.01) |
| H01L 51/50 | (2006.01) |

(52) U.S. Cl.
CPC ........ H01L 51/0073 (2013.01); C07D 209/86 (2013.01); C07D 307/91 (2013.01); C07D 333/76 (2013.01); C09K 11/025 (2013.01); H01L 51/0072 (2013.01); H01L 51/0074 (2013.01); H01L 51/5012 (2013.01)

(58) Field of Classification Search
None
See application file for complete search history.

(56) References Cited

U.S. PATENT DOCUMENTS

| 8,642,999 B2 * | 2/2014 | Shioya .................. C07C 13/567 257/40 |
| 2008/0093980 A1 | 4/2008 | Stoessel et al. |
| 2014/0158859 A1 * | 6/2014 | Fukuzaki ............ H01L 51/0056 250/200 |

FOREIGN PATENT DOCUMENTS

| JP | 2003-261473 A | | 9/2003 |
| JP | 2003261473 A | * | 9/2003 |
| JP | 2006-135146 A | | 5/2006 |
| JP | 2007-47806 A | | 2/2007 |
| JP | 2008-506657 A | | 3/2008 |
| JP | 2009-266927 A | | 11/2009 |
| JP | 2012-222255 A | | 11/2009 |
| KR | 10-2011-0079402 A | | 7/2011 |
| KR | 1020120013278 | * | 2/2012 |
| WO | WO 2006/005626 A2 | | 1/2006 |
| WO | WO 2012/141273 A1 | | 10/2012 |

OTHER PUBLICATIONS

CAPLUS printout of Foreign Patent No. KR2011079402, published on Jul. 7, 2011.*
CAPLUS printout of Foreign Patent No. CN103923637A, published on Jul. 16, 2014.*
Grant & Hackh's Chemical Dictionary (5th Ed. 1987) at p. 148.*
Zhou et al. Theoretical investigation on the one- and two-photo absorption properties of multi-branched oligomers with truxenone center and fluorene branches. Chemical Physics Letters, 2004, 397, 500-509.*
CAPLUS printout of "Korean Patent Application Publication No. 1020120013278, published on Feb. 14, 2012".*

(Continued)

*Primary Examiner* — Po-Chih Chen
(74) *Attorney, Agent, or Firm* — Lewis Roca Rothgerber Christie LLP

(57) ABSTRACT

A truxene derivative having good layer forming properties during layer formation and an organic electroluminescent device including the same. The truxene derivative may be represented by Formula 1:

Formula 1

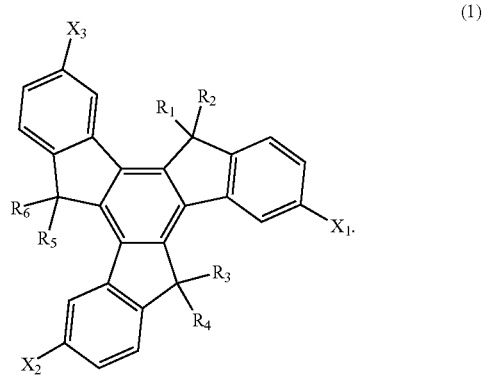

(1)

A layer including the truxene derivative in the organic electroluminescent device may have a decreased number or concentration of convex-concavo ( 凹凸 ) shapes, and performance limitations caused by non-uniformity in each layer of the organic electroluminescent device (for example, short circuiting or uneven light emission due to non-uniformity in an applied electric field) may be thereby prevented or reduced.

9 Claims, 1 Drawing Sheet

(56) References Cited

OTHER PUBLICATIONS

Machined-generated English translation of "Korean Patent Application Publication No. 1020120013278, published on Feb. 14, 2012".*
Raksasorn et al., Synthesis and characterization of hole-transporting star-shaped carbazolyl truxene derivatives. RSC Advances, 2015, 5, 72841-72848 (first published on Aug. 24, 2015).*
Machine English Translation of foreign patent publication No. JP2003261473A, published on Sep. 16, 2003.*
Gómez-Lor, B. et al., Synthesis of New $C_{3h}$ and $C_{3v}$ Truxene Derivatives, Eur. J. Org. Chem., 2001, pp. 2107-2114, WILEY-VCH Verlag GmbH, Weinheim, Germany.

* cited by examiner

TRUXENE DERIVATIVE AND ORGANIC ELECTROLUMINESCENCE DEVICE INCLUDING THE SAME

CROSS-REFERENCE TO RELATED APPLICATIONS

This application claims priority to and the benefit of Japanese Patent Application Nos. 2015-164108, filed on Aug. 21, 2015, and 2016-094230, filed on May 10, 2016, the entire content of each of which is hereby incorporated by reference.

BACKGROUND

One or more aspects of example embodiments of the present disclosure are related to a truxene derivative and an organic electroluminescence device, for example, an organic electroluminescent device including the same.

Recently, development on organic electroluminescent displays is being actively conducted. In addition, development on organic electroluminescent devices (which are self-luminescent devices used in organic electroluminescent displays) is also being actively conducted.

An example organic electroluminescent device may be obtained by laminating an anode, a hole injection layer, a hole transport layer, an emission layer, an electron transport layer, an electron injection layer, and a cathode one by one. In an organic electroluminescent device, holes and electrons injected from the anode and the cathode, respectively, may recombine in the emission layer to produce excitons. The organic electroluminescent device may emit light via transition (e.g., radiative decay) of the excitons to the ground state.

Various compounds have been examined as materials in each layer to improve the performance of an organic electroluminescent device. For example, truxene derivatives have been explored as materials for forming each layer of an organic electroluminescent device.

SUMMARY

However, truxene derivatives may have insufficient or unsuitable layer forming properties during layer formation using a coating method. When the layer forming properties during layer formation are insufficient or unsuitable, convex-concavo (凹凸) shapes may be generated on the surface of the layer, thereby forming a layer of uneven thickness. Accordingly, one or more performance limitations (for example, short circuiting or uneven light emission due to non-uniformity in an applied electric field) may be generated.

One or more aspects of example embodiments of the present disclosure are directed toward a truxene derivative having good layer forming properties during layer formation, and an organic electroluminescence device (e.g., an organic electroluminescent device) including the truxene derivative.

One or more example embodiments of the present disclosure provide a truxene derivative represented by Formula 1:

Formula 1

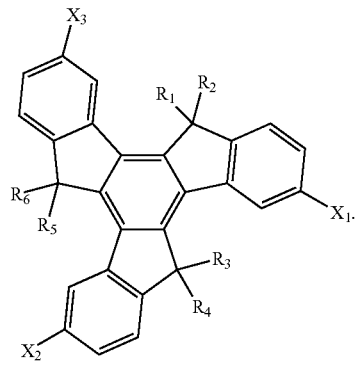

(1)

In Formula 1, $R_1$ to $R_6$ may each independently be hydrogen, a substituted or unsubstituted linear, branched, or cyclic alkyl group having 1 to 16 carbon atoms, a substituted or unsubstituted linear or branched alkoxy group having 1 to 16 carbon atoms, a substituted or unsubstituted aryl group having 6 to 36 carbon atoms for forming a ring, or a substituted or unsubstituted heterocyclic group having 3 to 32 carbon atoms for forming a ring; $X_1$ may be a substituted or unsubstituted dibenzofuranyl group, a substituted or unsubstituted dibenzothienyl group, a substituted or unsubstituted carbazolyl group, or a substituted or unsubstituted fluorenyl group; and $X_2$ and $X_3$ may each independently be hydrogen, a substituted or unsubstituted dibenzofuranyl group, a substituted or unsubstituted dibenzothienyl group, a substituted or unsubstituted carbazolyl group, or a substituted or unsubstituted fluorenyl group.

Accordingly, a truxene derivative having good layer forming properties during layer formation may be provided.

In one embodiment, $X_1$, $X_2$, and $X_3$ may be (e.g., may each represent) the same group.

Accordingly, the layer forming properties of the truxene derivative may be further improved, and the preparation of the truxene derivative may be relatively easy (e.g., be simplified).

In one embodiment, $X_1$, $X_2$, and $X_3$ may each independently be a substituted or unsubstituted dibenzofuranyl group, a substituted or unsubstituted dibenzothienyl group, a substituted or unsubstituted carbazolyl group, or a substituted or unsubstituted fluorenyl group; and $X_1$, $X_2$, and $X_3$ may each independently be combined (e.g., coupled) with the truxene skeleton via a benzene ring position.

Accordingly, a conjugation system may be formed between a truxene skeleton in the truxene derivative and $X_1$, $X_2$, and $X_3$ (e.g., electron conjugation may extend across the truxene skeleton, $X_1$, $X_2$, and $X_3$), and the electron donating function of the truxene derivative may increase.

In one embodiment, $R_1$ to $R_6$ may each independently be hydrogen, a substituted or unsubstituted linear, branched, or cyclic alkyl group having 1 to 7 carbon atoms, a substituted or unsubstituted linear or branched alkoxy group having 1 to 7 carbon atoms, or a substituted or unsubstituted aryl group having 6 to 12 carbon atoms for forming a ring.

Accordingly, the layer forming properties of the truxene derivative may be further improved.

In one embodiment, $R_1$ to $R_6$ may each independently be a linear alkyl group having 1 to 7 carbon atoms, a phenyl group, or an alkylphenyl group.

Accordingly, the layer forming properties of the truxene derivative may be further improved.

In one or more embodiments of the present disclosure, an organic electroluminescent device includes the truxene derivative.

Accordingly, a layer including the truxene derivative in the organic electroluminescent device may have a decreased number or concentration of convex-concavo (凹凸) shapes, and performance limitations caused by non-uniformity in each layer of the organic electroluminescent device (for example, short circuiting or uneven light emission due to non-uniformity in an applied electric field) may be thereby prevented or reduced.

In one embodiment, the organic electroluminescent device may include an emission layer, a hole transport layer, and/or a hole injection layer, wherein the emission layer, the hole transport layer, and/or the hole injection layer may include the truxene derivative.

Accordingly, short circuiting or uneven light emission due to non-uniformity in an applied electric field may be prevented or reduced, and the applied power may be used for emitting light without waste (e.g. may be used for efficiently emitting light), thereby improving the emission efficiency of the organic electroluminescent device.

BRIEF DESCRIPTION OF THE DRAWINGS

The accompanying drawings are included to enable further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
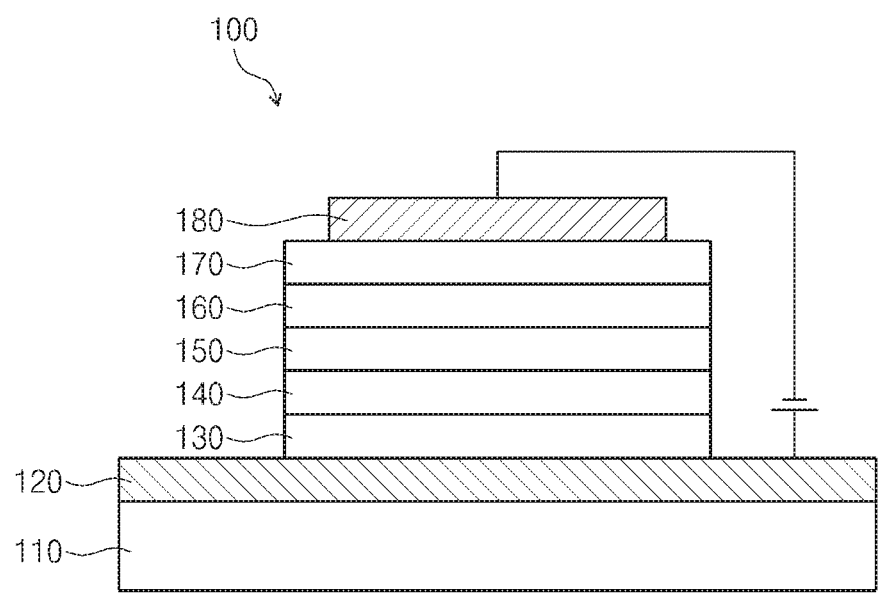
FIG. 1 is a schematic diagram illustrating the structure of an organic electroluminescent device according to an embodiment of the present disclosure.

Hereinafter, example embodiments of the present disclosure will be explained in more detail with reference to the accompanying drawings. The truxene derivative having good layer forming properties according to an embodiment of the present disclosure and the organic electroluminescence device (e.g., an organic electroluminescent device) including the truxene derivative may, however, be embodied in different forms and should not be construed as being limited to the example embodiments set forth herein.

In the description and drawings, elements having substantially the same functional configuration are designated with the same reference numeral, and repeated explanations thereof may not be provided. The thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

1. TRUXENE DERIVATIVE

First, the truxene derivative according to an embodiment of the present disclosure will be explained. The truxene derivative according to an embodiment of the present disclosure may be a compound represented by Formula 1:

Formula 1

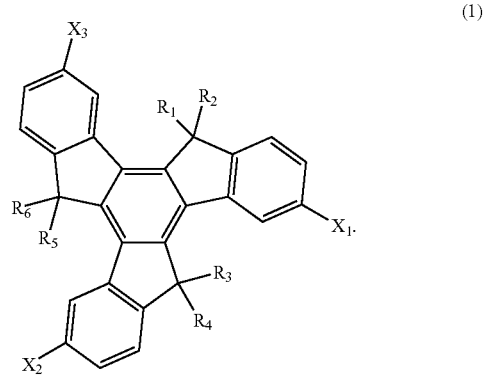

(1)

In Formula 1, $R_1$ to $R_6$ may each independently be hydrogen, a substituted or unsubstituted linear, branched, or cyclic alkyl group having 1 to 16 carbon atoms, a substituted or unsubstituted linear or branched alkoxy group having 1 to 16 carbon atoms, a substituted or unsubstituted aryl group having 6 to 36 carbon atoms for forming a ring, or a substituted or unsubstituted heterocyclic group having 3 to 32 carbon atoms for forming a ring. $X_1$ may be a substituted or unsubstituted dibenzofuranyl group, a substituted or unsubstituted dibenzothienyl group, a substituted or unsubstituted carbazolyl group, or a substituted or unsubstituted fluorenyl group. $X_2$ and $X_3$ may each independently be hydrogen, a substituted or unsubstituted dibenzofuranyl group, a substituted or unsubstituted dibenzothienyl group, a substituted or unsubstituted carbazolyl group, or a substituted or unsubstituted fluorenyl group.

The truxene derivative according to an embodiment of the present disclosure may have an amorphous structure in a formed layer. Therefore, the truxene derivative according to an embodiment of the present disclosure may have excellent layer forming properties during layer formation by a coating method, etc., and a layer including few (e.g., a low number or concentration of) surface convex-concavo (凹凸) shapes may be formed. Accordingly, performance limitations caused by non-uniformity in each layer of the organic electroluminescent device (for example, short circuiting or uneven light emission due to non-uniformity in an applied electric field) may be prevented or reduced.

In some embodiments, since the truxene derivative according to an embodiment of the present disclosure may have an amorphous structure within a formed layer, the layer may have flexibility and good following ability to the substrate (e.g., the layer may retain good adhesion to the substrate even under bending conditions), etc. Accordingly, the truxene derivative may be appropriately or suitably used in a flexible organic electroluminescent device.

In some embodiments, in the truxene derivative according to an embodiment of the present disclosure, a benzoheterole ring (such as a dibenzofuranyl group and/or a fluorenyl group) may be combined with the skeleton of the truxene. A compound having a truxene skeleton may have hole transport function and/or hole injection function; however, the group (e.g., the benzoheterole ring) may provide the truxene derivative with appropriate or suitable electron donating function, and as a result, the truxene derivative may have polarity. In the case where such a truxene derivative (e.g., a truxene derivative bonded with a benzoheterole ring) is used in an organic electroluminescent device, the charge balance of holes and electrons in the device may be appropriately or suitably controlled, and the emission efficiency of the organic electroluminescent device may be improved. In some embodiments, by combining $X_1$-$X_3$ at a certain position of the truxene skeleton, steric complexity in the truxene derivative may be relatively decreased, and as a result, the truxene derivative may be chemically stable.

The use of the truxene derivative according to an embodiment of the present disclosure is not limited thereto. For example, the truxene derivative may be appropriately or suitably used as the host material, the hole transport material, or the hole injection material of an emission layer in an organic electroluminescent device.

In Formula 1, in $R_1$ to $R_6$, the number of carbons in the linear, branched, or cyclic alkyl group may be in the above-described range, and in some embodiments, 1 to 12, and in some embodiments, 1 to 7. The number of carbons in the linear or branched alkyl group may be 1 to 6, and in some embodiments, 1 to 4. The number of carbons in the cyclic alkyl group may be in the above-described range, and in some embodiments, 3 to 7, and in some embodiments, 4 to 7. In some embodiments, among the linear, branched, or cyclic alkyl, the linear or branched alkyl may be preferable, and in some embodiments the linear alkyl may be more preferable.

In $R_1$ to $R_6$, non-limiting example embodiments of the linear, branched, or cyclic alkyl group may include a linear alkyl group (such as a methyl group, an ethyl group, a propyl group, a butyl group, an octyl group, a decyl group, and/or a pentadecyl group), a branched alkyl group (such as a t-butyl group), and a cycloalkyl group (such as a cyclobutyl group, a cyclopentyl group, a cyclohexyl group, and/or a cycloheptyl group).

In $R_1$ to $R_6$, the number of carbons in the linear or branched alkoxy carbon may be within the above-described range, and in some embodiments, 1 to 12, in some embodiments, 1 to 7, in some embodiments, 1 to 6, and in some embodiments, 1 to 4. Non-limiting example embodiments of the alkoxy group may include a linear alkoxy group (such as a methoxy group, an ethoxy group, a propoxy group, a butoxy group, an octyloxy group, a decyloxy group, and/or a pentadecyloxy group), and a branched alkoxy group (such as a t-butoxy group).

The number of carbon atoms for forming a ring in the aryl group may be in the above-described range, and in some embodiments, 6 to 18, in some embodiments, 6 to 12, and in some embodiments, 4 to 7. Non-limiting examples of the aryl group may include a monocyclic aromatic group (such as a phenyl group), a non-condensed polycyclic aromatic group (such as a biphenyl group, a terphenyl group, a fluoranthenyl group, and/or a triphenylenyl group), and a condensed polycyclic aromatic group (such as a naphthyl group, an anthryl group, a phenanthryl group, a fluorenyl group, an indenyl group, a pyrenyl group, and/or an acetonaphthenyl group).

The number of carbon atoms for forming a ring in the heterocyclic group may be in the above-described range, and in some embodiments, 4 to 18, and in some embodiments, 5 to 12.

The heterocyclic group may include, for example, a heteroaryl group or a non-aromatic heterocyclic group.

The heteroaryl group may include, for example, a monocyclic heteroaryl group (such as a pyridyl group, a furanyl group, a pyranyl group, a thienyl group, a quinolyl group, and/or an isoquinolyl group) and a polycyclic heteroaryl group (such as a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, and/or a dibenzothienyl group).

Non-limiting examples of the non-aromatic heterocycle may include pyrrolidinyl, tetrahydrofuranyl, tetrahydrothiophenyl, tetrahydropyranyl, tetrahydrothiopyranyl, piperidinyl, 1,4-dioxanyl, 1,4-oxathianyl, morpholinyl, 1,4-dithianyl, piperazinyl, and 1,4-azathianyl.

$R_1$ to $R_6$ may each independently be hydrogen, a substituted or unsubstituted, linear, branched, or cyclic alkyl group having 1 to 7 carbon atoms, a substituted or unsubstituted linear or branched alkoxy group having 1 to 7 carbon atoms, or a substituted or unsubstituted aryl group having 6 to 12 carbon atoms for forming a ring. In some embodiments, $R_1$ to $R_6$ may be a linear alkyl group having 1 to 7 carbon atoms, a phenyl group, or an alkylphenyl group, and in some embodiments, a methyl group, an ethyl group, a n-propyl group, a phenyl group, or a methylphenyl group.

$X_2$ and $X_3$ may each independently be the same groups as described in connection with Formula 1, and in some embodiments, may each independently be a substituted or unsubstituted dibenzofuranyl group, a substituted or unsubstituted dibenzothienyl group, a substituted or unsubstituted carbazolyl group, or a substituted or unsubstituted fluorenyl group. Due to the groups (e.g., the presence of $X_2$ and $X_3$), the electron donating function of the truxene derivative may be sufficient or suitable. When the truxene derivative is included in an emission layer, electron injection and/or hole injection to the emission layer may be good or suitable.

In some embodiments, all of $X_1$ to $X_3$ may be combined (e.g., coupled) with the truxene skeleton. A conjugation system may be formed between the truxene skeleton in the truxene derivative and $X_1$ to $X_3$ (e.g., electron conjugation may extend across the truxene skeleton, $X_1$, $X_2$, and $X_3$), and the electron donating function of the truxene derivative may increase.

For example, $X_1$ to $X_3$ may each independently include a substituted or unsubstituted dibenzofuran-1-yl, dibenzofuran-2-yl, dibenzofuran-3-yl, or dibenzofuran-4-yl, a substituted or unsubstituted dibenzothiophen-1-yl, dibenzothiophen-2-yl, dibenzothiophen-3-yl, or dibenzothiophen-4-yl, a substituted or unsubstituted carbazol-1-yl, carbazol-2-yl, carbazol-3-yl, or carbazol-4-yl, or a substituted or unsubstituted fluoren-1-yl, fluoren-2-yl, fluoren-3-yl, or fluoren-4-yl. In some embodiments, $X_1$-$X_3$ may each independently include a substituted or unsubstituted dibenzofuran-2-yl or dibenzofuran-4-yl, a substituted or unsubstituted dibenzothiophen-2-yl or dibenzothiophene-4-yl, a substituted or unsubstituted carbazol-3-yl, or a substituted or unsubstituted fluorene-2-yl or fluorene-4-yl.

In some embodiments, $X_1$ to $X_3$ may not make a bond (e.g., may not be coupled) with the truxene skeleton via a benzene ring position. For example, $X_1$ to $X_3$ may each independently be a substituted or unsubstituted carbazol-9-yl, or a substituted or unsubstituted fluoren-9-yl.

$X_1$ to $X_3$ may be different from each other, but in some embodiments, at least two thereof may be the same group, and in some embodiments, all three may be (e.g., may simultaneously be) the same group. In this case, the structure of the truxene derivative may be stable, and the preparation of the truxene derivative may be relatively easy and simple.

Each group represented by $X_1$ to $X_3$ and $R_1$ to $R_6$ may each independently be substituted by, for example, a cyano group, a silyl group, a mono-, di-, or tri-alkylsilyl group having 1 to 10 carbon atoms, a linear, branched or cyclic alkyl group having 1 to 16 carbon atoms, a linear or branched alkoxy group having 1 to 16 carbon atoms, an aryl group having 6 to 36 carbon atoms for forming a ring, a heterocyclic group having 3 to 32 carbon atoms for forming a ring, etc., without specific limitation. Any hydrogen position in an unsubstituted $X_1$ to $X_3$ and $R_1$ to $R_6$ group may be substituted with the substituent to form each substituted $X_1$ to $X_3$ and $R_1$ to $R_6$ group. In each group represented by $X_1$ to $X_3$ and $R_1$ to $R_6$, in the case where at least two hydrogen atoms are substituted, a cyclic alkyl group, an aryl group, and/or a heterocyclic group may be formed including the substituent and an atom combined with the substituent. In this case, the substituent may form a condensed structure with the truxene skeleton.

Examples of each substituent and their preferable carbon number, etc. are not specifically limited; however, the substituents may be the same as for each group of $R_1$ to $R_6$.

In particular, the substituent of $X_1$ to $X_3$ may each independently be a linear or branched alkyl group having 1 to 6 carbon atoms, or an aryl group having 4 to 18 carbon atoms for forming a ring (such as a methyl group, an ethyl group, a propyl group, a t-butyl group, a phenyl group, and/or a benzene ring formed (e.g., condensed or fused) with the benzene ring of $X_1$-$X_3$), and in some embodiments, a methyl group or a phenyl group.

The substituent may be substituted at any position of each group of $X_1$ to $X_3$ and $R_1$ to $R_6$.

The truxene derivative according to an embodiment of the present disclosure may include at least one of Compounds 1-29 (collectively represented as Compound Group 1). In some embodiments, the truxene derivative may be selected from Compounds 1, 18, 22, and 24. However, embodiments of the truxene derivative are not limited to the following compounds:

Compound Group 1

1

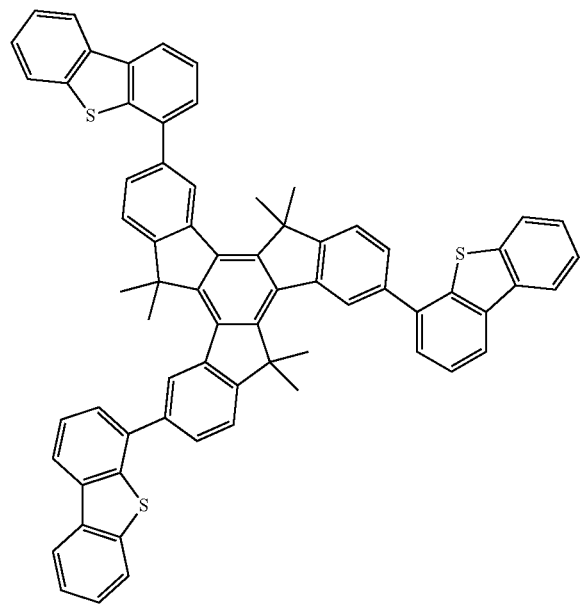

2

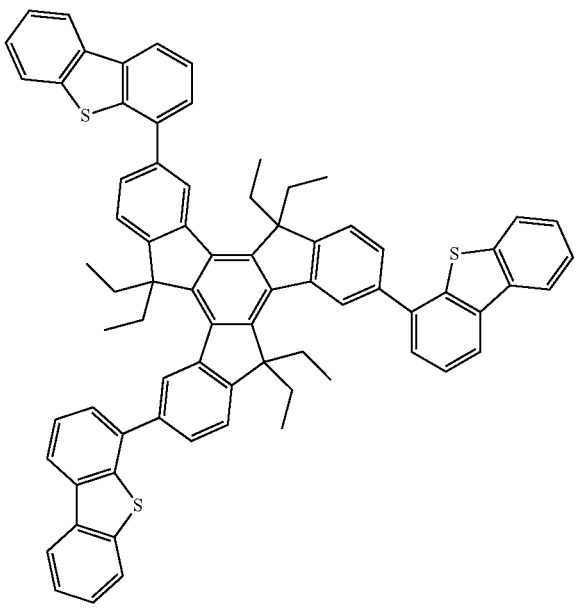

3

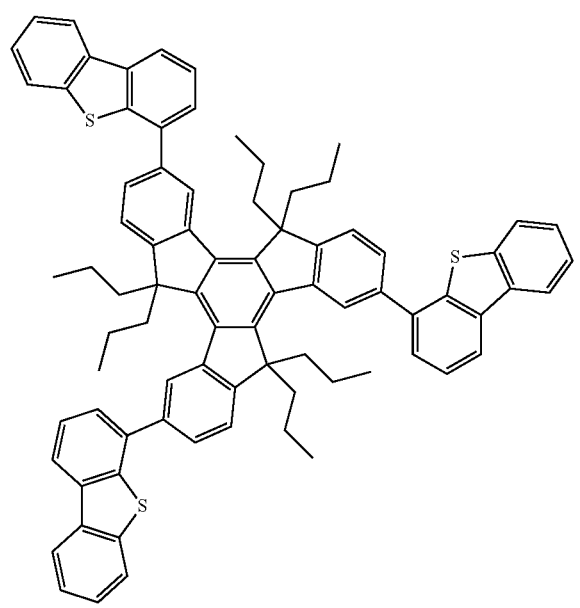

4

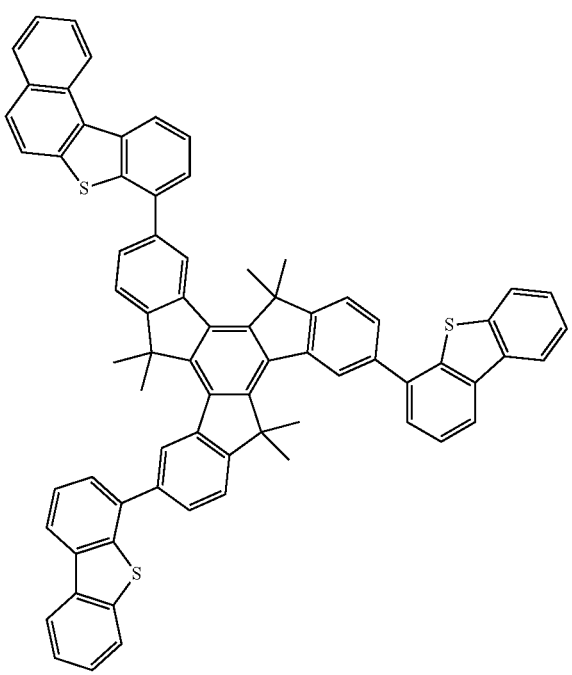

-continued
5
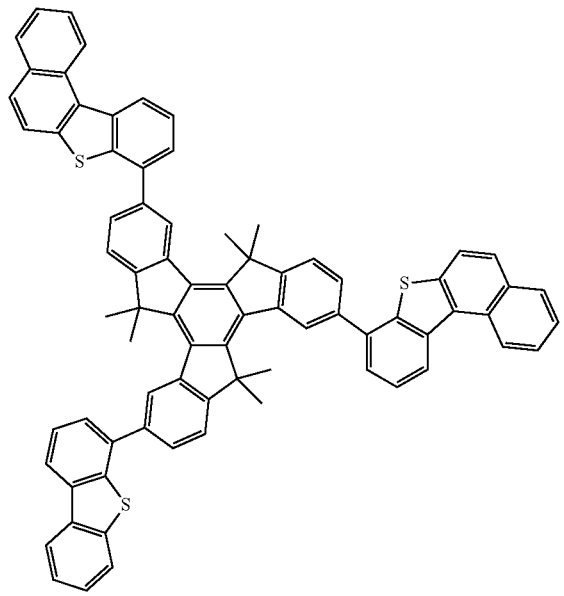
6
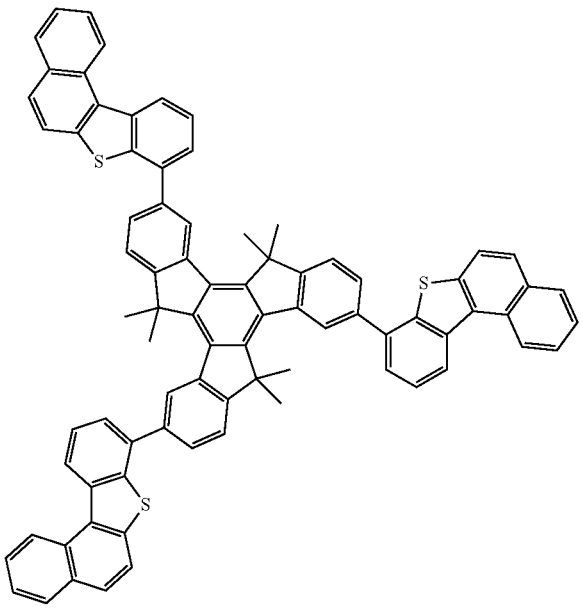
7
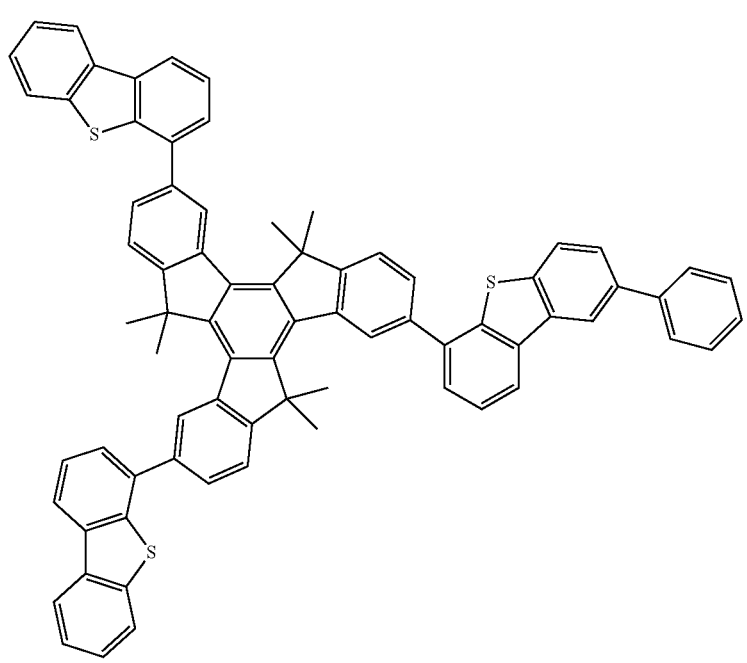

8
9
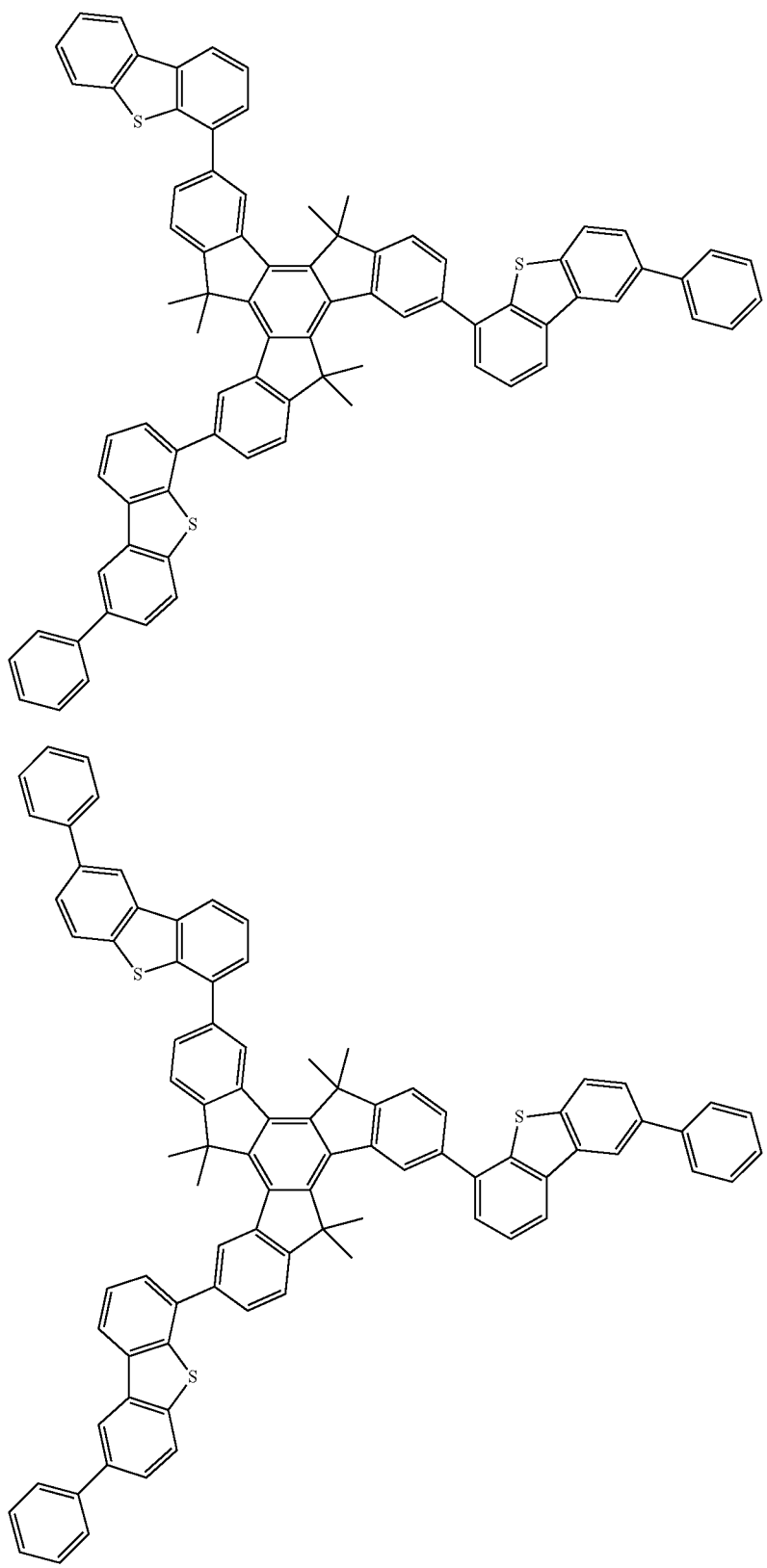

10
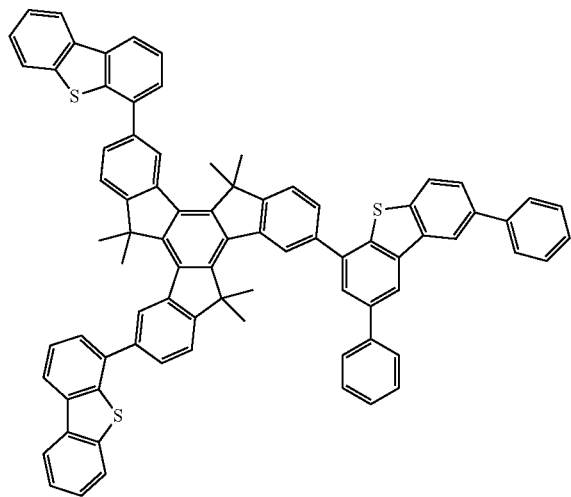
11
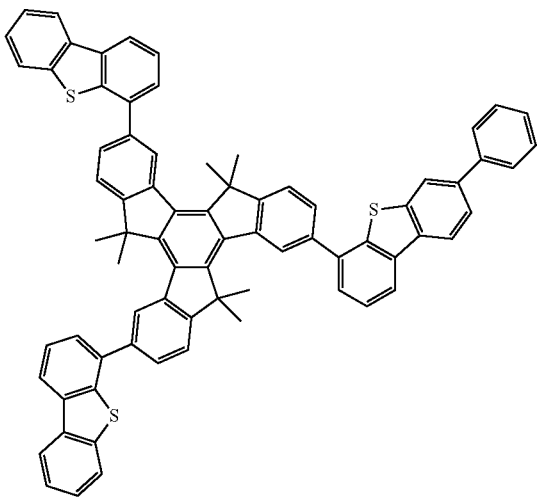
12
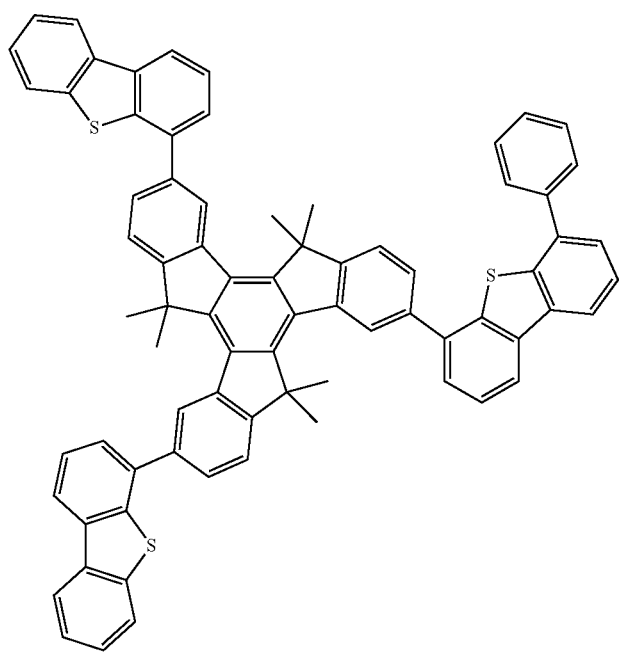

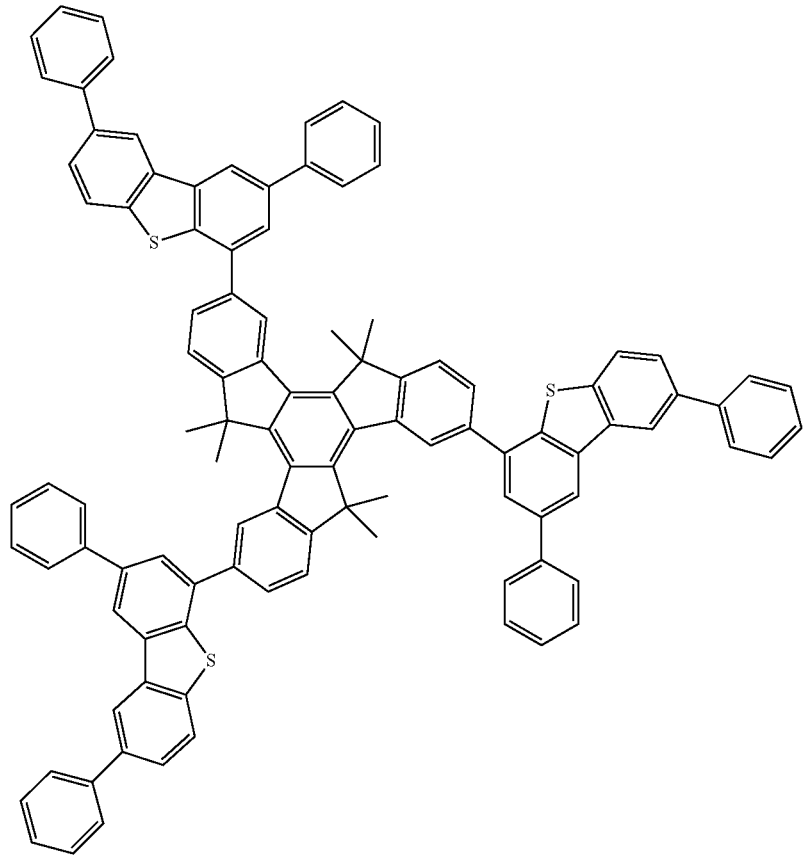
13
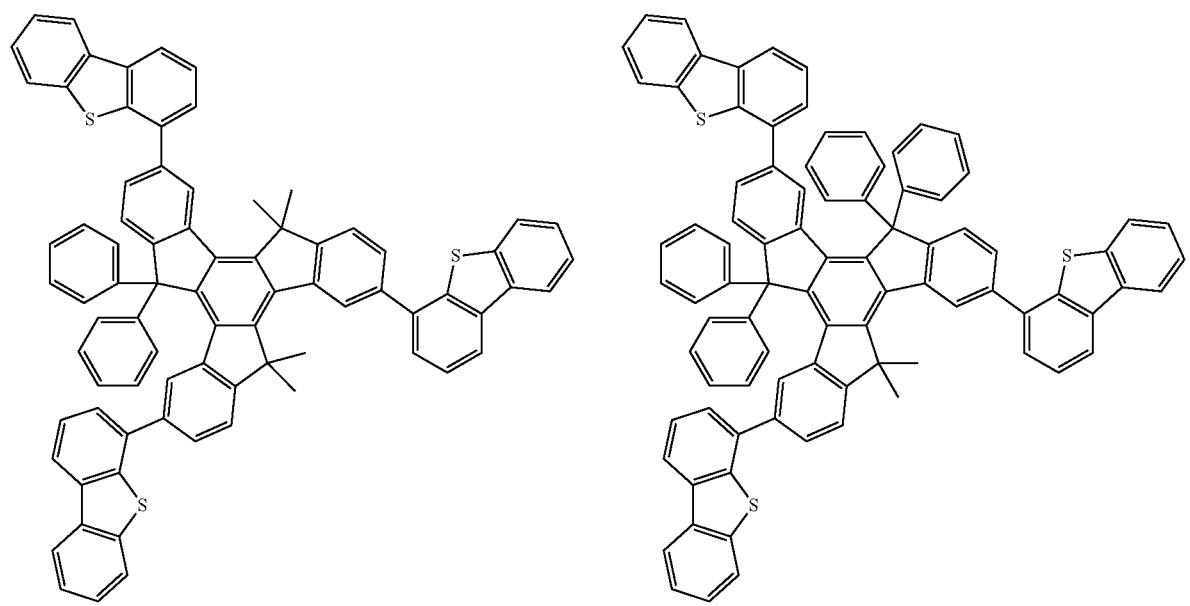
14
15

-continued
16
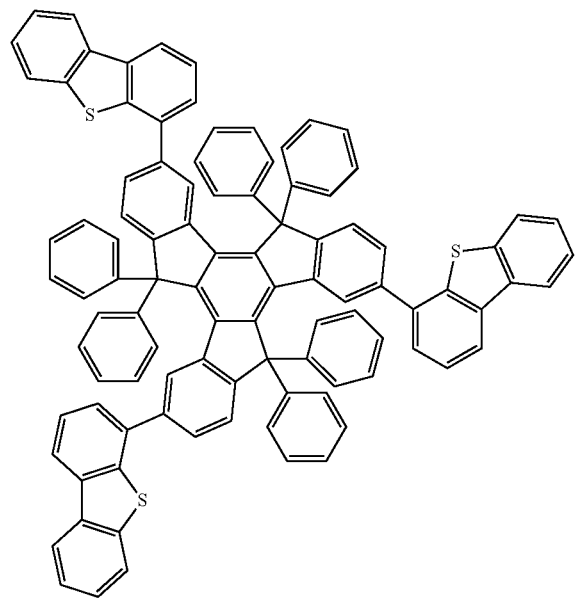
17
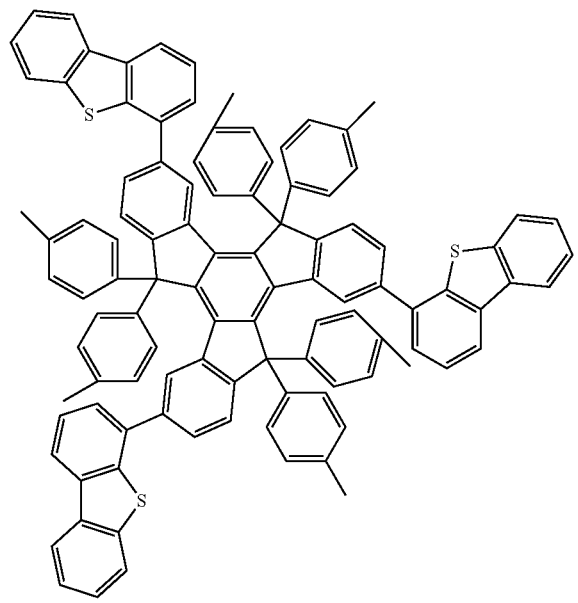
18
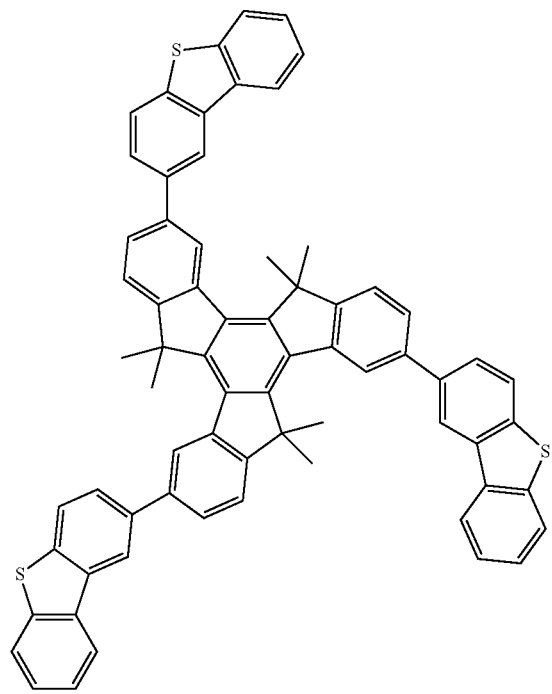
19
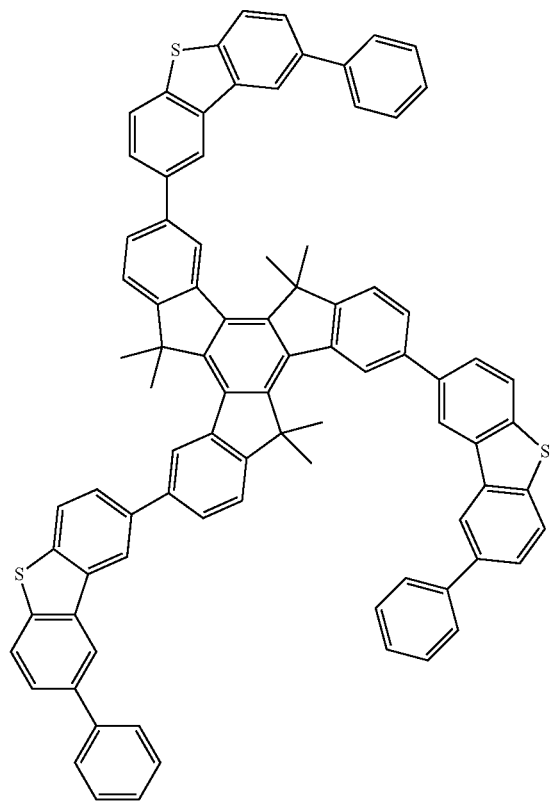

20
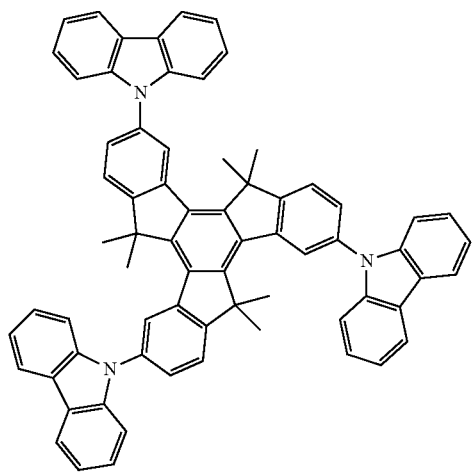
21
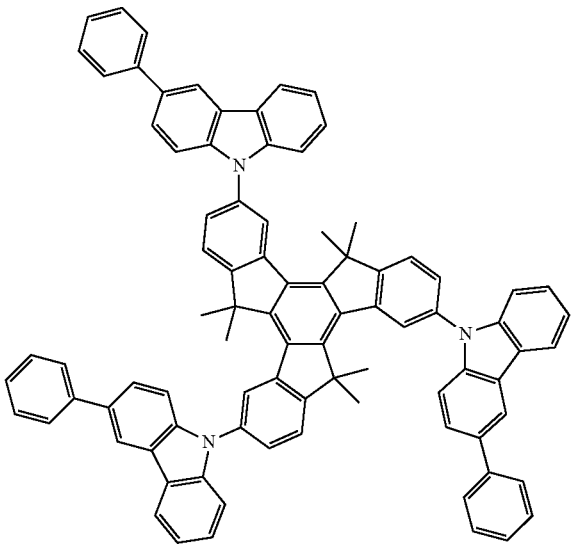
22
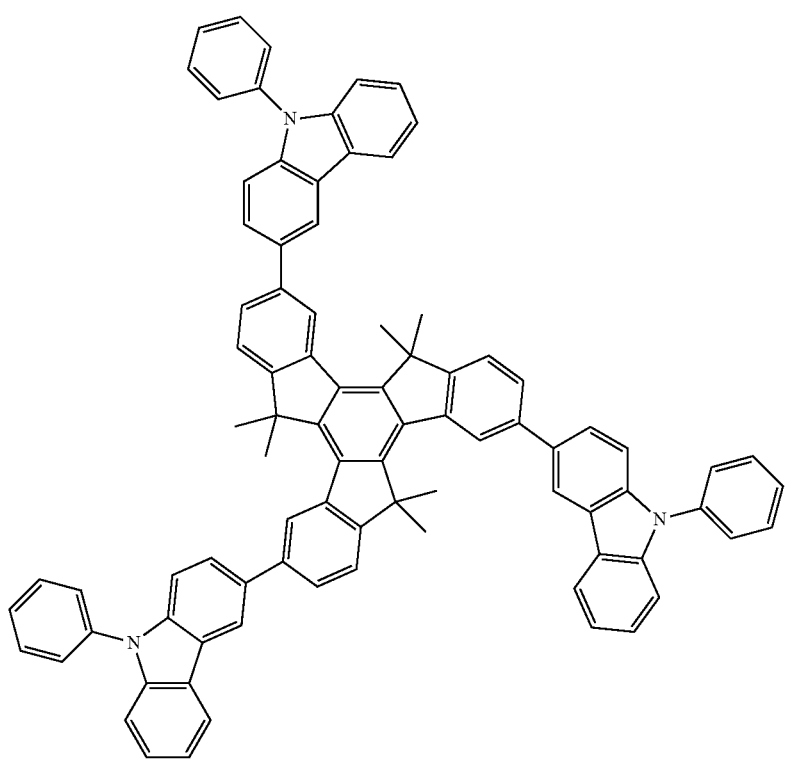

23
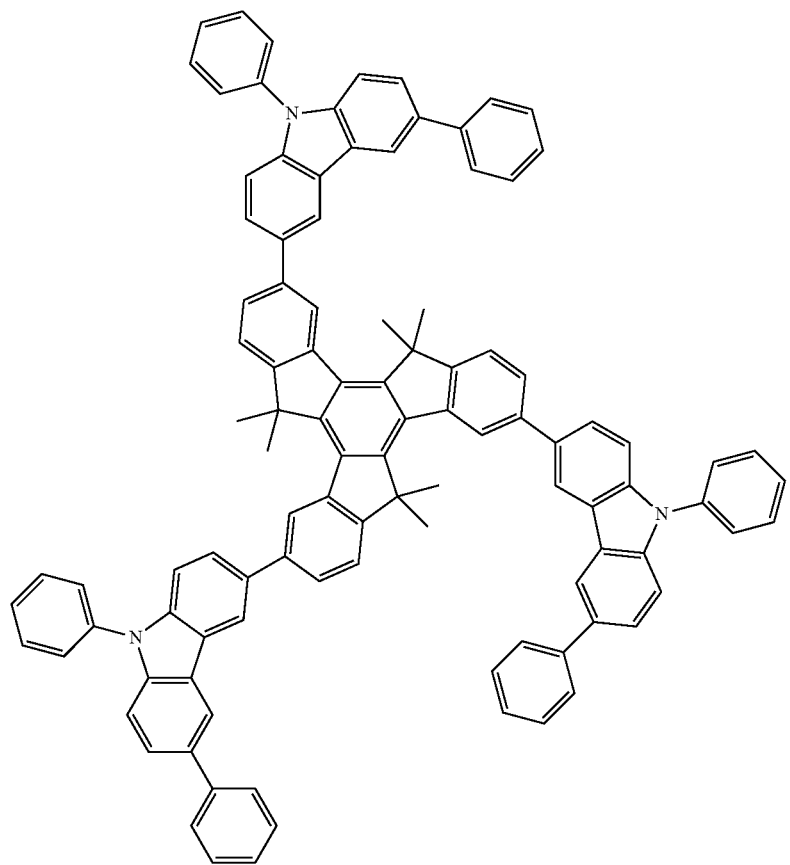
24
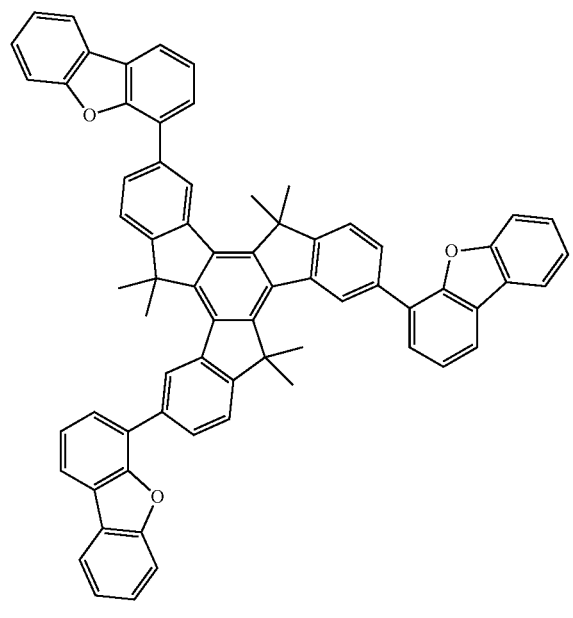
25
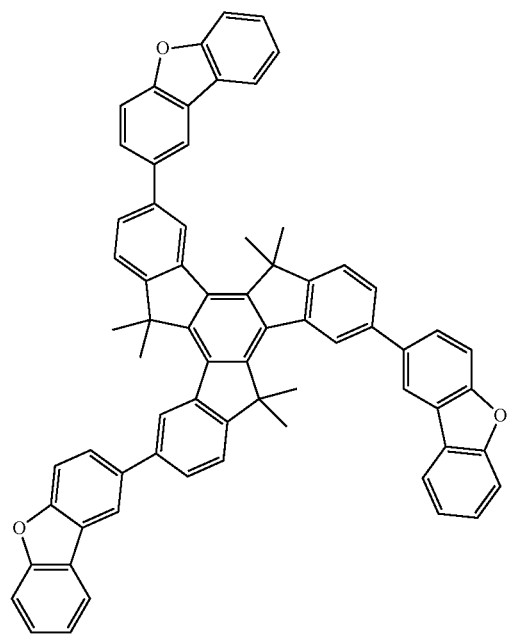

26

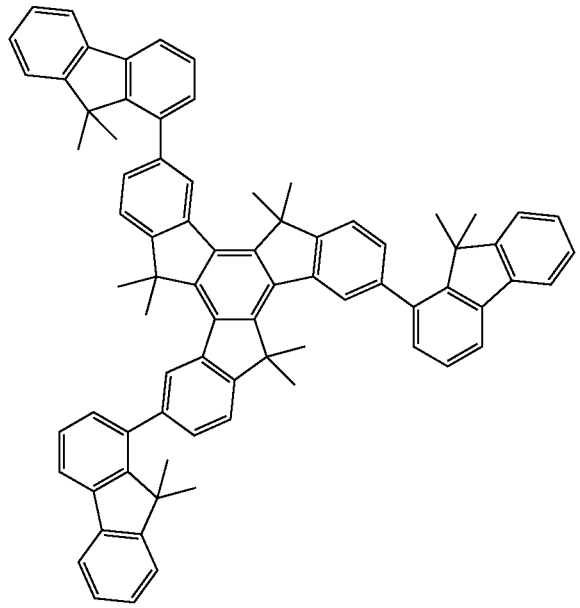

27

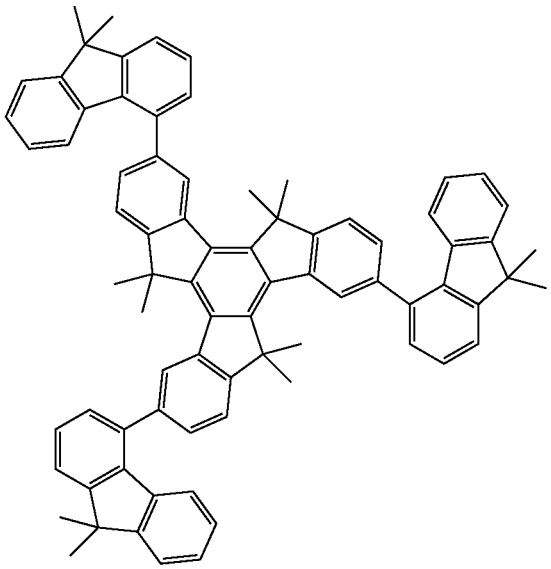

28

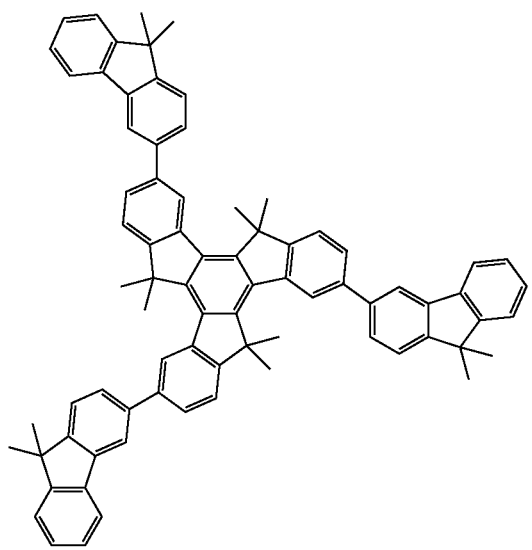

29

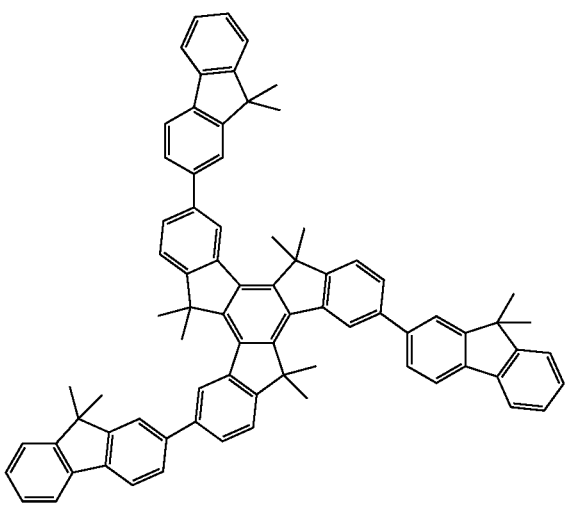

The truxene derivative according to an embodiment of the present disclosure has been explained in detail. When the truxene derivative according to an embodiment of the present disclosure has an amorphous structure within a formed layer, its layer forming properties may be good or suitable, and a layer with few surface convex-concavo (凹凸) shapes may be formed. The layer formed may be flexible and may have good following ability to a substrate (e.g., may retain good adhesion to the substrate even under bending conditions), etc. The truxene derivative according to an embodiment of the present disclosure may have good hole injection function and hole transport function as well as appropriate or suitable bipolar properties. Accordingly, when the truxene derivative according to an embodiment of the present disclosure is used as a hole transport material, a hole injection material, and/or a host material in an emission layer, charge balance in an organic electroluminescent device may be appropriately or suitably controlled, and the emission efficiency of the organic electroluminescent device may be improved.

The truxene derivative according to an embodiment of the present disclosure may be prepared using any suitable method, without specific limitation.

2. ORGANIC ELECTROLUMINESCENT DEVICE

Referring to FIG. 1, an organic electroluminescent device using the truxene derivative according to an embodiment of the present disclosure will be explained in more detail. FIG. 1 is a schematic diagram illustrating the structure of an organic electroluminescent device according to an embodiment of the present disclosure.

As shown in FIG. 1, an organic electroluminescent device 100 according to an embodiment of the present disclosure may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

The truxene derivative according to an embodiment of the present disclosure may be included in, for example, the hole injection layer 130, the hole transport layer 140, and/or the emission layer 150. A layer including the truxene derivative may be planarized or uniform (e.g., substantially planarized and/or substantially uniform). Accordingly, for example, short circuiting or uneven light emission due to non-uniformity in an applied electric field may be prevented or reduced, and the power applied may be used for emitting light without waste (e.g. may be used for efficiently emitting light), thereby relatively improving the emission efficiency of the organic electroluminescent device 100. In some embodiments, the truxene derivative according to an embodiment of the present disclosure may be included in the emission layer 150. However, embodiments of the layer including the truxene derivative are not limited thereto. For example, the truxene derivative may be included in any organic layer between the first electrode 120 and the second electrode 180.

The substrate 110 may be any substrate suitably used in an organic electroluminescent device. For example, the substrate 110 may be a glass substrate, a semiconductor substrate, or a transparent plastic substrate.

The first electrode 120 may be formed on the substrate 110. The first electrode 120 may be an anode, and may be formed as a transmission type (e.g., transmissive) electrode using a metal, an alloy, a conductive compound, etc., each having a high work function. For example, the first electrode 120 may be formed using indium tin oxide ($In_2O_3$—$SnO_2$: ITO), indium zinc oxide ($In_2O_3$—ZnO), tin oxide ($SnO_2$), zinc oxide (ZnO), etc., each having good transparency and/or conductivity. In some embodiments, the first electrode 120 may be formed as a reflection type (e.g., reflective) electrode by laminating magnesium (Mg), aluminum (Al), etc. on the transparent conductive layer.

On the first electrode 120, the hole injection layer 130 may be formed. The hole injection layer 130 may facilitate easy injection of holes from the first electrode 120 and may be formed to a thickness of about 10 nm to about 150 nm.

The hole injection layer 130 may be formed using the truxene derivative. In some embodiments, in the case where the truxene derivative according to an embodiment of the present disclosure is included in another layer, the hole injection layer 130 may be formed using, for example, a compound represented by the following structures or hole transport materials (collectively referred to as Formula 2):

Formula 2

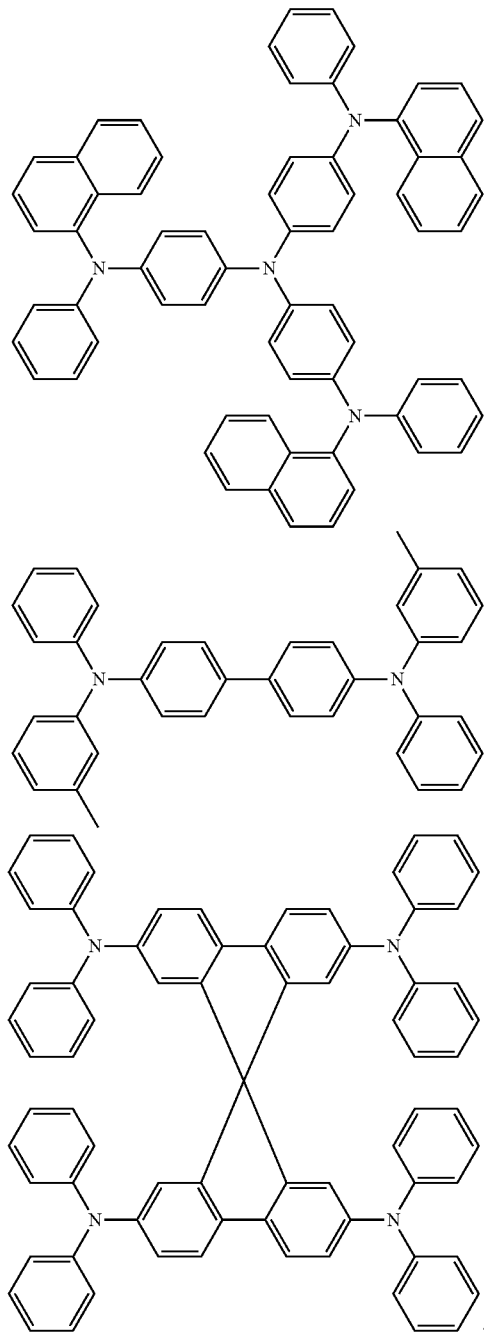

The hole transport materials capable of forming the hole injection layer 130 may include, for example, triphenylamine-containing polyether ketone (TPAPEK), 4-isopropyl-4'-methyldiphenyliodiniumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound (such as copper phthalocyanine), 4,4',4"-tris(3-methylphenylphenylamino)triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-TNATA), polyaniline/dodecylbenzenesulfonic acid (PANI/DBSA), poly(3,4-ethylenedioxythiophene)/poly(4- styrenesulfonate) (PEDOT/PSS), polyaniline/camphor sulfonic acid (PANI/CSA), polyaniline/poly(4-styrenesulfonate) (PANI/PSS), etc.

The hole transport layer 140 may be formed on the hole injection layer 130. The hole transport layer 140 may facilitate easy transport of holes and may be formed to a thickness of about 10 nm to about 150 nm. In some embodiments, the hole transport layer 140 may be formed as a plurality of layers.

The hole transport layer 140 may be formed by including the truxene derivative according to an embodiment of the present disclosure. In the case where the truxene derivative according to an embodiment of the present disclosure is included in another layer, the hole transport layer 140 may be formed using any suitable hole transport material. The hole transport material may include, for example, 1,1-bis[(di-4-tolylamino)phenyl]cyclohexane (TAPC), a carbazole derivative (such as N-phenylcarbazole and/or polyvinylcarbazole), N,N'-bis(3-methylphenyl)-N,N'-diphenyl-[1,1-biphenyl]-4,4'-diamine (TPD), 4,4',4''-tris(N-carbazolyl)triphenylamine (TCTA), N,N'-di(1-naphthyl)-N,N'-diphenylbenzidine (NPB), etc.

The emission layer 150 may be formed on the hole transport layer 140. The emission layer 150 may emit light via fluorescence or phosphorescence, and may be formed to a thickness of about 10 nm to about 60 nm. The emission layer 150 may be formed as a mixture (e.g., mixed) layer of a dopant material and a host material. For example, the emission layer 150 may be formed as a mixture (e.g., mixed) layer doped with the dopant material in a weight amount ratio of about 0.1 wt % to 50 wt %, and in some embodiments, about 0.1 wt % to 20 wt % on the basis of the total weight amount of the host material.

The host material and the dopant material included in the emission layer 150 may include any suitable host materials and dopant materials. For example, the emission layer 150 may include a fluoranthene derivative, pyrene and derivatives thereof, an acetylene derivative, a fluorene derivative, perylene and derivatives thereof, a chrysene derivative, or a styryl derivative, etc. as the host material and/or the dopant material. For example, the emission layer 150 may include tris(8-quinolinolato)aluminum (Alq$_3$), 4,4'-N,N'-dicarbazole-biphenyl (CBP), poly(n-vinylcarbazole) (PVK), 4,4',4''-tris(N-carbazolyl)triphenylamine (TCTA), 1,3,5-tris(N-phenylbenzimidazol-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dm-CBP), bis(2,2-diphenylvinyl)-1,1'-biphenyl (DPVBi), 1,4-bis(2-(3-N-ethylcarbazolyl)vinyl)benzene (BCzVB), 4-(di-p-tolylamino)-4'-((di-p-tolylamino)styryl)stilbene (DPAVB), N-(4-((E)-2-(6-((E)-4-(diphenylamino)styryl)naphthalene-2-yl)vinyl)phenyl)-N-phenylbenzeneamine (N-BDAVBi), 2,5,8,11-tetra-tert-butylperylene (TBPe), 1,1-dipyrene, 1,4-dipyrenylbenzene, 1,4-bis(N,N-diphenylamino)pyrene, etc. as the host material and/or the dopant material.

In some embodiments, the emission layer 150 may be formed as an emission layer that may emit light of a specific color. For example, the emission layer 150 may be formed as a red emitting layer, a green emitting layer, or a blue emitting layer.

In the case where the emission layer 150 is the blue emitting layer, any suitable blue dopant may be used. For example, perylene and derivatives thereof and an iridium (Ir) complex (such as bis[2-(4,6-difluorophenyl)pyridinate]picolinate iridium(III) (Flrpic)) may be used as a blue dopant.

In the case where the emission layer 150 is a red emitting layer, any suitable red dopant may be used. For example, rubrene and derivatives thereof, 4-dicyanomethylene-2-(p-dimethylaminostyryl)-6-methyl-4H-pyrane (DCM) and derivatives thereof, an iridium complex (such as bis(1-phenylisoquinoline)(acetylacetonate) iridium(III) (Ir(piq)$_2$(acac)), an osmium (Os) complex, a platinum complex, etc. may be used as a red dopant.

In the case where the emission layer 150 is the green emitting layer, any suitable green dopant may be used. For example, Coumarin and derivatives thereof, and an iridium complex (such as tris[2-(para-tolyppyridine]iridium(III) (Ir(mppy))$_3$, tris(2-phenylpyridine) iridium(III) (Ir(ppy)$_3$), etc.) may be used.

The host material may include the truxene derivative according to an embodiment of the present disclosure. In the case where the truxene derivative according to an embodiment of the present disclosure is included in another layer, the host material may include any suitable host material.

In some embodiments, the host material may be a mixture of two or more compounds. For example, the host material may include a compound having electron transport function or hole transport function, in addition to a compound (which may be the main component of the host material) to control the charge balance of the organic electroluminescent device 100.

In the case where the emission layer 150 includes the truxene derivative according to an embodiment of the present disclosure as the main component of the host material, a compound having electron transport function may be further included as the host material. In this case, the charge balance of the organic electroluminescent device 100 may be more highly controlled, and emission efficiency may be further improved. Embodiments of the compound having such electron transport function are not specifically limited; however, it may be selected from electron transport materials other than the compounds used as the host material, which will be explained later. Non-limiting examples of the compound having electron transport function that may be used as the host material may include a quinolinol derivative, an imidazole derivative, and a pyridine derivative. For example, tris(8-quinolinolato) aluminum (Alq$_3$), 1,3,5-tris(N-phenylbenzimidazol-2-Abenzene (TPBI), 1,3-bis[2-(2,2'-bipyridine-6-yl)-1,3,4-oxadiazo-5-yl]benzene, 3,3',5,5'-tetra[(m-pyridyl)-phenyl-3-yl]biphenyl, etc. may be used.

In this case, the host material may include the truxene derivative according to an embodiment of the present disclosure and the compound having electron transport function in a weight ratio (e.g., of the truxene derivative to the compound having electron transport function) of 20:1 to 1:4, and in some embodiments, 10:1 to 1:1.

The electron transport layer 160 may be formed on the emission layer 150. The electron transport layer 160 is a layer having electron transport function and may be formed to a thickness of about 15 nm to about 50 nm. The electron transport layer 160 may be formed using, for example, a compound represented by the following structures (collectively referred to as Formula 3):

Formula 3

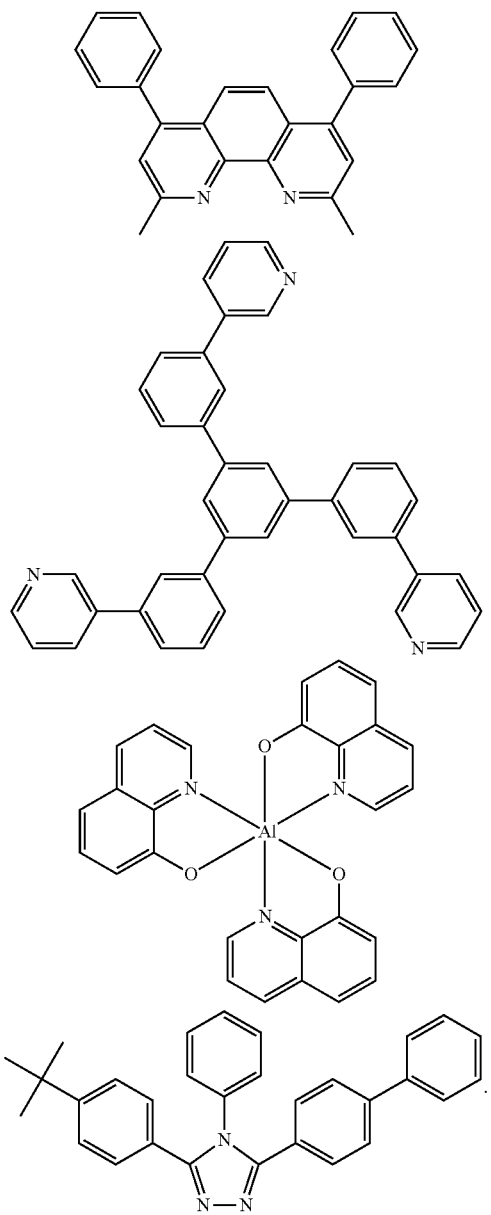

The electron transport layer 160 may be formed using any suitable electron transport material. Non-limiting examples of the electron transport material may include tris(8-quinolinato) aluminum (Alq$_3$), a material having a nitrogen-containing aromatic ring, etc. Non-limiting examples of the nitrogen-containing aromatic ring may include an oxydiazole derivative (such as 2-(4-tert-butylphenyl)-5-(4-biphenylyl)-1,3,4-oxydiazole), a compound including a pyridine ring (such as 1,3,5-tri[(3-pyridyl)-phen-3-yl]benzene), a compound including a triazine ring (such as 2,4,6-tris(3'-(pyridin-3-yl)biphenyl-3-yl)-1,3,5-triazine), a compound including an imidazole ring (such as 2-(4-(N-phenylbenzimidazolyl-1-ylphenyl)-9,10-dinaphthylanthracene)), etc.

The electron injection layer 170 may be formed on the electron transport layer 160. The electron injection layer 170 may facilitate easy injection of electrons from the second electrode 180 and may be formed to a thickness of about 0.3 nm to about 9 nm. The electron injection layer 170 may be formed using any material that may be suitably used to form the electron injection layer 170. For example, the electron injection layer 170 may be formed using a lithium complex (such as lithium 8-quinolinato (LiQ) and/or lithium fluoride (LiF)), sodium chloride (NaCl), cesium fluoride (CsF), lithium oxide (Li$_2$O), barium oxide (BaO), etc.

The second electrode 180 may be formed on the electron injection layer 170. The second electrode 180 may be, for example, a cathode, and may be formed as a reflection type (e.g., reflective) electrode using a metal, an alloy, or a conductive compound having a low work function. The second electrode 180 may be formed using, for example, a metal (such as lithium (Li), magnesium (Mg), aluminum (Al), and/or calcium (Ca)), or a metal mixture (such as aluminum-lithium (Al—Li), magnesium-indium (Mg—In), and/or magnesium-silver (Mg—Ag)). In some embodiments, the second electrode 180 may be formed as a transmission type (e.g., transmissive) electrode using a thin film of the metal material with a thickness of about 20 nm or less, or a transparent conductive layer of indium tin oxide or indium zinc oxide.

Each of the above-described layers may be formed by selecting an appropriate or suitable layer forming method according to the material to be used (such as vacuum deposition, sputtering, and/or other suitable coating methods). Each organic layer between the first electrode 120 and the second electrode 180 may be formed using one or more suitable deposition methods, coating methods, etc. An amorphous and planar layer may be formed using the truxene derivative represented by Formula 1 even when using a coating method that may be generally prone to crystal formation. Therefore, a layer including the truxene derivative may have good or suitable planarity and substantial uniformity when compared to a layer formed using compounds in the related art. In some embodiments, a metal layer (such as the first electrode 120 and/or the second electrode 180) may be formed by, for example, a vacuum deposition method, a sputtering method, etc.

An organic electroluminescent device 100 according to an embodiment of the present disclosure has been explained in detail. In the organic electroluminescent device 100, a layer including the truxene derivative according to an embodiment of the present disclosure may have a decreased concentration or number of surface convex-concavo (凹凸) shapes, and performance limitations caused by non-uniformity in each layer of the organic electroluminescent device (for example, short circuiting or uneven light emission due to non-uniformity in an applied electric field) may be prevented or reduced. In some embodiments, through the inclusion of the truxene derivative represented by Formula 1, the organic electroluminescent device 100 according to an embodiment of the present disclosure may have appropriately or suitably controlled charge balance in the organic electroluminescent device 100, thereby attaining good or suitable emission efficiency.

Figure 2:
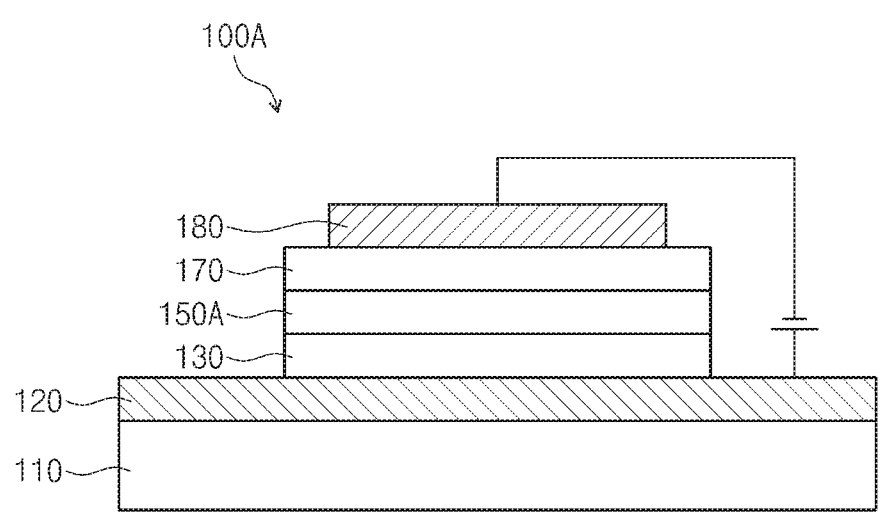
FIG. 2 is a schematic diagram illustrating the structure of an organic electroluminescent device according to another embodiment of the present disclosure.

An organic electroluminescent device according to another embodiment of the present disclosure will be explained in more detail. FIG. 2 is a schematic diagram illustrating the structure of an organic electroluminescent device according to another embodiment of the present disclosure.

As shown in FIG. 2, an organic electroluminescent device 100A may include a substrate 110, a first electrode 120 on the substrate 110, a hole injection layer 130 on the first electrode 120, an emission layer 150A on the hole injection layer 130, an electron injection layer 170 on the emission layer 150A, and a second electrode 180 on the electron injection layer 170.

Here, the substrate 110, the first electrode 120, the hole injection layer 130, the electron injection layer 170, and the second electrode 180 may each have the same configuration as each corresponding element in the organic electroluminescent device 100.

The emission layer 150A may emit light via fluorescence or phosphorescence and may be formed to a thickness of about 10 nm to about 200 nm, and in some embodiments, about 1 nm to about 100 nm. The emission layer 150A may include the truxene derivative. The emission layer 150A may be formed, for example, as a mixture layer of a dopant material and a host material. For example, the emission layer 150A may be formed as a mixture layer doped with the dopant material in a weight ratio of about 0.1 wt % to 50 wt %, and in some embodiments, 0.1 wt % to 20 wt % of the total weight of the host material. In this case, the truxene derivative may be used as the host material.

The host material may be added to the truxene derivative and may include another compound. The emission layer 150A may further include, for example, a compound having electron transport function as the host material. In this case, the charge balance of the organic electroluminescent device 100 may be controlled even further, and emission efficiency may be improved (e.g., increased). The compound having such electron transport function may be the same as that described in connection with the emission layer 150, and the ratio of the truxene derivative to the compound in the host material may be the same as described above.

An embodiment of the organic electroluminescent device 100A has been explained in detail. Since the number or concentration of surface convex-concavo (凹凸) shapes on the surface of the emission layer 150A may decrease in the organic electroluminescent device 100A according to an embodiment of the present disclosure, performance limitations caused by non-uniformity in the emission layer 150A of the organic electroluminescent device 100A (for example, short circuiting or uneven light emission due to non-uniformity in an applied electric field) may be prevented or reduced. In some embodiments, through the inclusion of the truxene derivative represented by Formula 1, the organic electroluminescent device 100A according to an embodiment of the present disclosure may attain appropriately or suitably controlled charge balance, thereby accomplishing good emission efficiency.

Example embodiments of the laminated structures of the organic electroluminescent devices 100 and 100A are not limited to the above-described embodiments. The organic electroluminescent devices 100 and 100A may be formed with other suitable laminated structures. For example, the organic electroluminescent device 100 may exclude at least one layer among the hole injection layer 130, the hole transport layer 140, the electron transport layer 160, and the electron injection layer 170, or may include another layer. Each layer in the organic electroluminescent devices 100 and 100A may be formed as a single layer or as a plurality of layers.

In some embodiments, the organic electroluminescent device 100 may include a hole blocking layer between the hole transport layer 140 and the emission layer 150 to prevent or reduce diffusion of triplet excitons and/or holes to the electron transport layer 160. The hole blocking layer may be formed using, for example, an oxadiazole derivative, a triazole derivative, a phenanthroline derivative, etc.

3. EXAMPLES

Hereinafter, a truxene derivative and an organic electroluminescent device including the truxene derivative according to example embodiments of the present disclosure will be explained in more detail by referring to examples and comparative examples. However, the following embodiments are provided only for purposes of illustration, and embodiments of the truxene derivative and the organic electroluminescent device are not limited thereto.

Synthesis of Truxene Derivative

First, truxene derivatives were synthesized according to the methods described below.

(A) Materials

Commercially available reagent grade starting materials, reagents, and solvents were used for synthesis without further purification. Dehydrated tetrahydrofuran (THF) was used as is. Spherical silica gel (neutral) was purchased from Kanto Chemical Co., Ltd. and used as a filler (e.g., substrate) for column chromatography.

3,8,13-tribromo-10,15-dihydro-5H-diindeno[1,2-a:1',2'-c]fluorene was synthesized according to the method described in B. Gomez-Lor, et al., Eur. J. Org. Chem. 2001, 2107-2114.

(B) Identification Method

The identification of each synthesized compound was conducted using nuclear magnetic resonance ($^1$H NMR) spectroscopy and mass spectrometry (MS). $^1$H NMR spectra were measured using a Joel J NM-ECX400 spectrometer (400 MHz) or a Joel J NM-ECS400 spectrometer (400 MHz). MS specimens were ionized using a matrix-assisted laser desorption/ionization (MALDI) method using α-cyano-4-hydroxycinnamic acid (CHCA) as a matrix, and MS spectra were measured using time of flight (TOF) mass spectroscopy (MALDI-TOF-MS). The MALDI-TOF-MS measurements were conducted using a Shimadzu-Kratos AXIMA-CFR PLUS TOF mass spectrometer.

(C) Synthesis

Synthetic Example 1

Synthesis of Ph3-Tr (Comparative Example)

A compound (Ph3-Tr) represented by Formula 4 was synthesized using the following procedure:

Formula 4

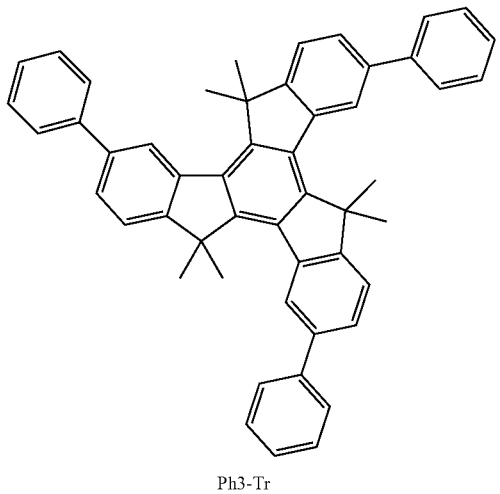

Ph3-Tr (i) Synthesis of Br3-Tr

First, prior to preparing Ph3-Tr, an intermediate Br3-Tr was synthesized by the following mechanism (Formula 5):

Formula 5

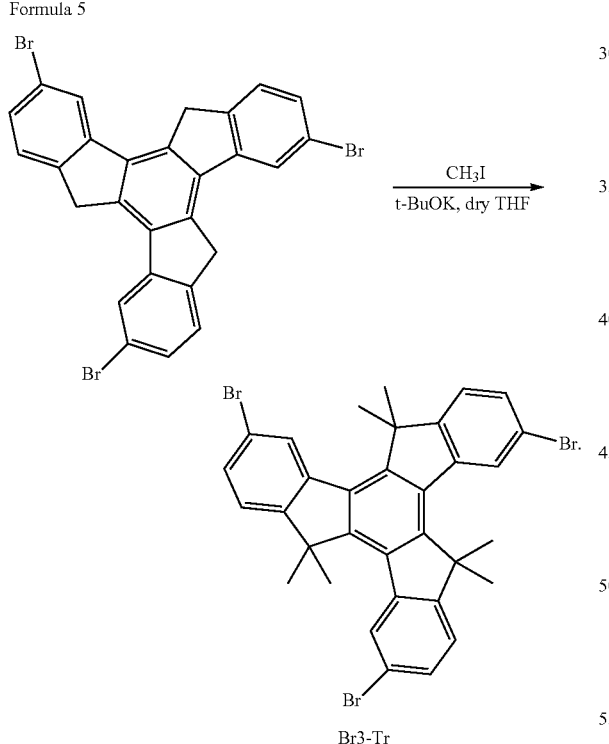

Br3-Tr

A 50 mL, two-necked flask was dried, and a solution of 3,8,13-tribromo 10,15-dihydro-5H-diindeno[1,2-a:1',2'-c] fluorene (another name: 3,8,13-truxene) (116 mg, 0.200 mmol) in dehydrated THF (5.0 mL) was added thereto, followed by stirring in an ice bath. Potassium t-butoxide (180 mg, 1.60 mmol) was added thereto, and the color of the solution changed from lemon yellow to dark red. After stirring for about 1 hour, iodomethane (283 mg, 2.00 mmol) was slowly added and stirred for about 2 additional hours. After that, additional amounts of potassium t-butoxide (180 mg, 1.60 mmol) and iodomethane (283 mg, 2.00 mmol) were added according to the same procedure, and the ice bath was removed, followed by stirring for about 12 hours at room temperature. After the reaction was complete, the solvents were evaporated from the reaction, chloroform was added to the remaining solids, and the insoluble materials were removed by filtration. The filtrate was concentrated under vacuum and separated by silica gel column chromatography (developing solution: chloroform/hexane=1/2 by volume) to produce Br3-Tr (75.0 mg, 0.113 mmol, 57%) as an ivory powder.

$^1$H NMR (400 MHz, CDCl$_3$): δ 8.36 (d, J=1.8 Hz, 3H), 7.51 (dd, J=7.9 and 1.8 Hz, 3H), 7.40 (d, J=7.9 Hz, 3H), 1.83 (s, 18H); $^{13}$C NMR (100 MHz, CDCl$_3$): δ 156.13, 149.34, 138.53, 134.89, 129.98, 128.58, 124.09, 120.28, 46.84, 23.92; MALDI-TOF MS (m/z): [M+2] calc. for C$_{33}$H$_{27}$Br$_3$, 661.96. found, 661.96.

(ii) Synthesis of Ph3-Tr

Ph3-Tr was synthesized according to the following mechanism (Formula 6):

Formula 6

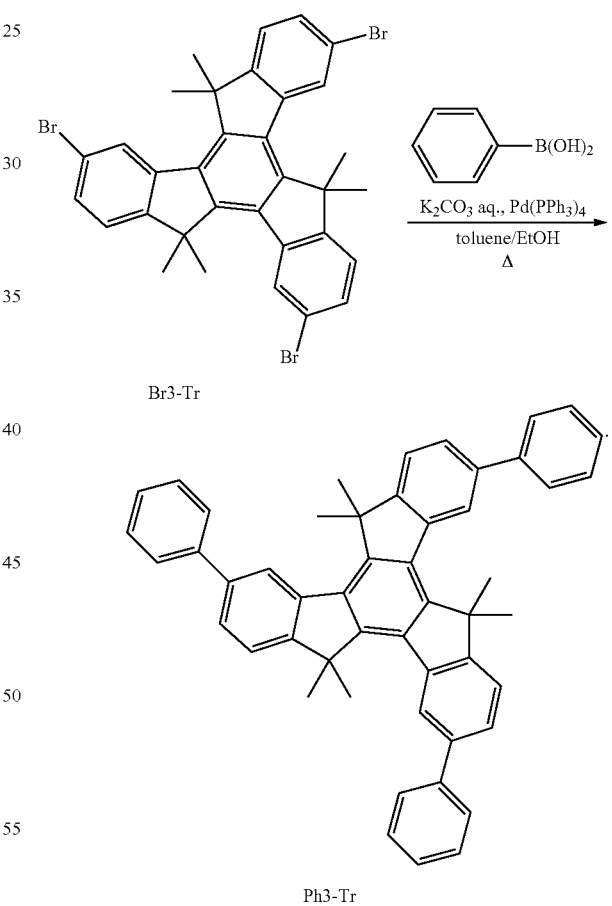

Ph3-Tr

Br3-Tr (332 mg, 0.501 mmol), phenylboronic acid (305 mg, 2.50 mmol), and tetrakis(triphenylphosphine)palladium (0) (57.8 mg, 0.0500 mmol) were added to a mixture of toluene (17.5 mL) and ethanol (4.0 mL), and the reaction vessel was filled with nitrogen. Potassium carbonate (691 mg, 5.00 mol) dissolved in water (4.0 mL) was added thereto, and the mixture thus obtained was heated and stirred for about 15 hours at about 80° C. The reaction mixture was allowed to cool to room temperature and then concentrated by removing the solvents under reduced pressure. The residue was extracted with chloroform and water using a separatory funnel, and the organic layer thus obtained was dried over magnesium sulfate and filtered. The solvents were distilled under reduced pressure. The crude product thus obtained was separated by silica gel column chromatography (developing solution: chloroform/hexane=1/2 by volume) and recrystallized using a mixture of hexane and ethyl acetate to produce Ph3-Tr as a white solid (88.0 mg, 0.134 mmol, 27%).

$^1$H NMR (400 MHz, CDCl$_3$): δ 8.56 (s, 3H), 7.74 (dd, J=7.9 and 1.4 Hz, 6H), 7.64 (dd, J=7.3 and 1.4 Hz, 3H), 7.62 (d, J=7.3 Hz, 3H), 7.54 (t, J=7.3 Hz, 3H), 7.42 (t, J=7.3 Hz, 3H), 2.00 (s, 18H); $^{13}$C NMR (100 MHz, CDCl$_3$): δ 156.66, 148.83, 142.07, 139.61, 137.34, 135.68, 128.96, 127.32, 127.13, 126.15, 124.67, 122.70, 46.75, 24.28; MALDI-TOF MS (m/z): M$^+$ calc. for C$_{51}$H$_{42}$, 654.33. found, 654.09.

Synthetic Example 2

Synthesis of Compound 1 (Example)

Compound 1 was synthesized according to the following mechanism (Formula 7):

Formula 7

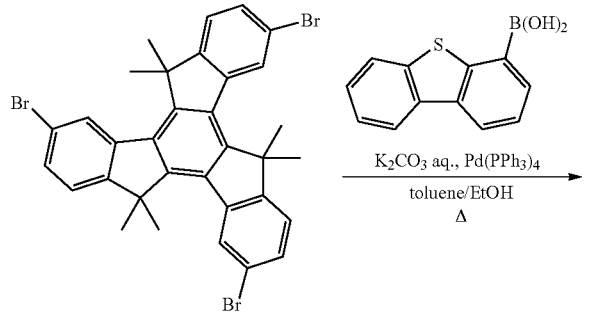

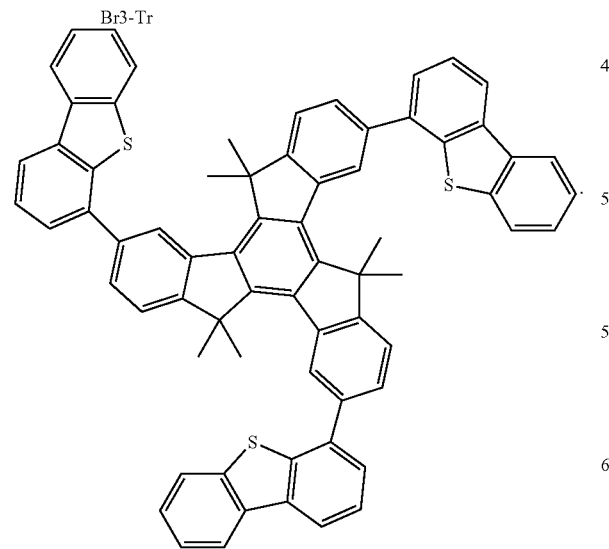

Br3-Tr (133 mg, 0.201 mmol), dibenzo[b,d]thiophene-4-ylboronic acid (205 mg, 0.899 mmol), and tetrakis(triphenylphosphine)palladium(0) (23.4 mg, 0.0202 mmol) were added to a mixture of toluene (7.1 mL) and ethanol (1.6 mL), and the reaction vessel was filled with nitrogen. Potassium carbonate (276 mg, 2.00 mol) dissolved in water (1.6 mL) was added thereto, and the mixture thus obtained was heated and stirred for about 20 hours at a temperature of 80° C. or less. The reaction mixture was allowed to cool to room temperature and concentrated by removing the solvents under reduced pressure. The residue was extracted with chloroform and water using a separatory funnel, and the organic layer thus obtained was dried over magnesium sulfate and filtered. The solvents were distilled under reduced pressure. The crude product thus obtained was separated by silica gel column chromatography (developing solution: chloroform/hexane=2/3 by volume) and recrystallized from a mixture of hexane and ethyl acetate to produce Compound 1 as a white solid (142 mg, 0.146 mmol, 73%).

$^1$H NMR (400 MHz, CDCl$_3$): δ 8.66 (d, J=1.4 Hz, 3H), 8.26-8.22 (m, 6H), 7.88 (dd, J=7.3 and 1.4 Hz, 3H), 7.74 (dd, J=7.7 and 1.4 Hz, 3H), 7.67-7.61 (m, 9H), 7.53-7.47 (m, 6H), 2.00 (s, 18H); $^{13}$C NMR (100 MHz, CDCl$_3$): δ 157.51, 149.32, 139.81, 138.96, 138.86, 137.97, 137.43, 136.37, 136.01, 135.69, 127.33, 127.30, 126.90, 125.60, 125.36, 124.53, 122.91, 122.82, 121.89, 120.44, 47.02, 24.43; MALDI-TOF MS (m/z): M$^+$ calc. for C$_{69}$H$_{48}$S$_3$, 972.29. found, 972.29.

Synthetic Example 3

Synthesis of Compound 18 (Example)

Compound 18 was synthesized according to the following mechanism (Formula 8):

Formula 8

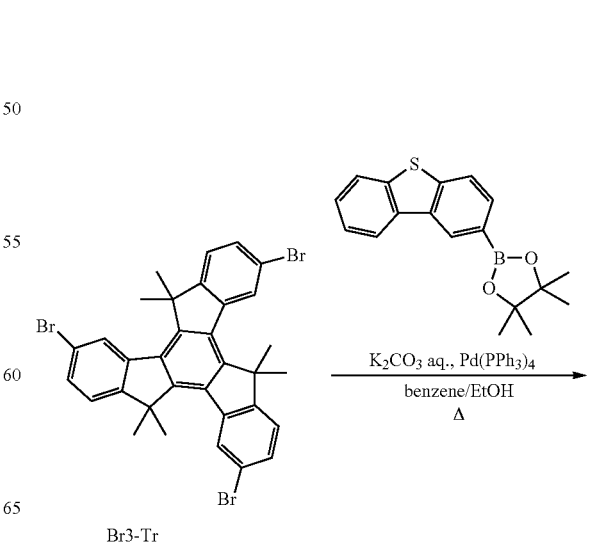

-continued

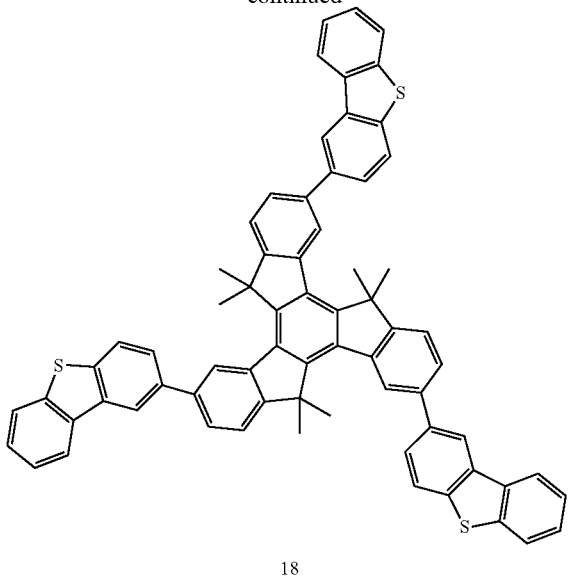

18

Br3-Tr (265 mg, 0.400 mmol), 2-(dibenzo[b,d]thiophene-2-yl)-4,4,5,5-tetramethyl-1,3,2-dioxabororane (496 mg, 1.60 mmol), and tetrakis(triphenylphosphine)palladium(0) (46.2 mg, 0.0400 mmol) were added to a mixture of benzene (14 mL) and ethanol (3.2 mL), and the reaction vessel was filled with nitrogen. Potassium carbonate (544 mg, 4.00 mol) dissolved in water (3.2 mL) was added thereto, and the mixture thus obtained was heated and stirred for about 14 hours at the temperature of 80° C. or less. The reaction mixture was allowed to cool to room temperature and concentrated by removing solvents under reduced pressure. The residue was extracted with chloroform and water using a separatory funnel, and the organic layer thus obtained was dried over magnesium sulfate and filtered. The solvents were distilled under reduced pressure. The crude product thus obtained was separated by silica gel column chromatography (developing solution: chloroform/hexane=1/2 by volume) and recrystallized from ethyl acetate to produce Compound 18 as a white solid (219 mg, 0.225 mmol, 56%).

$^1$H NMR (400 MHz, CDCl$_3$): δ 8.70 (s, 3H), 8.49 (d, J=1.4 Hz, 3H), 8.26 (d, J=7.7 Hz, 3H), 7.81 (dd, J=8.7 and 1.8 Hz, 3H), 7.77 (dd, J=7.7 and 1.3 Hz, 3H), 7.68-7.62 (m, 15H), 7.58 (d, J=8.6 Hz, 3H), 7.54-7.43 (m, 9H), 7.37-7.33 (m, 3H), 2.07 (s, 18H); $^{13}$C NMR (100 MHz, CDCl$_3$): δ 156.13, 148.94, 141.50, 140.50, 140.43, 137.82, 137.54, 135.92, 134.50, 130.04, 127.63, 127.21, 126.39, 126.29, 125.79, 125.07, 124.10, 123.63, 122.77, 120.46, 120.18, 119.00, 110.33, 110.07, 46.88, 24.48; MALDI-TOF MS (m/z): M$^+$ calc. for C$_{87}$H$_{63}$N$_3$, 1149.50. found, 1149.20.

Synthetic Example 4

Synthesis of Compound 22 (Example)

Compound 22 was synthesized according to the following mechanism (Formula 9):

Formula 9

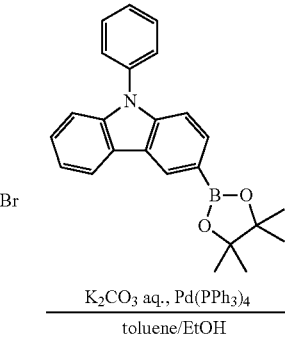

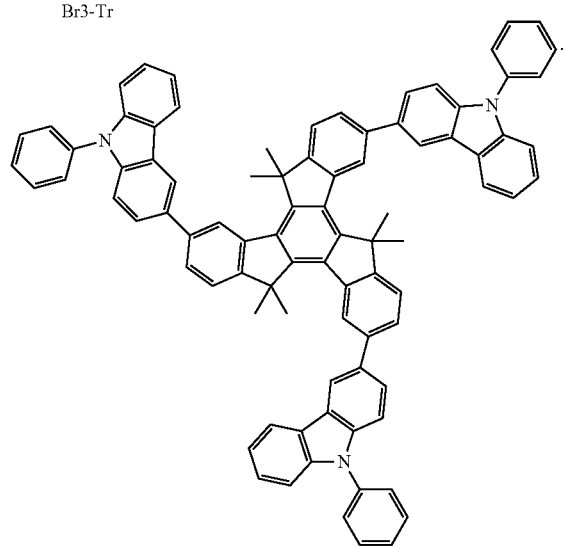

22

Br3-Tr (133 mg, 0.201 mmol), 9-phenyl-3-(4,4,5,5-tetramethyl-1,3,2-dioxabororane-2-yl)-9H-carbazole (295 mg, 0.80 mmol), and tetrakis(triphenylphosphine)palladium (0) (23.3 mg, 0.0202 mmol) were added to a mixture of toluene (7.1 mL) and ethanol (1.6 mL), and the reaction vessel was filled with nitrogen. Potassium carbonate (276 mg, 4.00 mol) dissolved in water (1.6 mL) was added thereto, and the mixture thus obtained was heated and stirred for about 18 hours at a temperature of 80° C. or less. The reaction mixture was allowed to cool to room temperature and was concentrated under reduced pressure. The residue was extracted with chloroform and water using a separatory funnel, and the organic layer thus obtained was dried with magnesium sulfate and then filtered. The solvents were distilled under reduced pressure. The crude product thus obtained was separated by silica gel column chromatography (developing solvent: chloroform/hexane=1/2 by volume), and the solid thus obtained was dispersed in an appropriate or suitable amount of methanol and filtered under suction to produce Compound 22 as a white solid (88.0 mg, 0.0765 mmol, 38%).

$^1$H NMR (400 MHz, CDCl$_3$): δ 8.70 (s, 3H), 8.49 (d, J=1.4 Hz, 3H), 8.26 (d, J=7.7 Hz, 3H), 7.81 (dd, J=8.7 and 1.8 Hz, 3H), 7.77 (dd, J=7.7 and 1.3 Hz, 3H), 7.68-7.62 (m, 15H), 7.58 (d, J=8.6 Hz, 3H), 7.54-7.43 (m, 9H), 7.37-7.33 (m, 3H), 2.07 (s, 18H); $^{13}$C NMR (100 MHz, CDCl$_3$): δ 156.13, 148.94, 141.50, 140.50, 140.43, 137.82, 137.54, 135.92, 134.50, 130.04, 127.63, 127.21, 126.39, 126.29, 125.79, 125.07, 124.10, 123.63, 122.77, 120.46, 120.18, 119.00, 110.33, 110.07, 46.88, 24.48; MALDI-TOF MS (m/z): M$^+$ calc. for C$_{87}$H$_{63}$N$_3$, 1149.50. found, 1149.20.

Synthetic Example 5

Synthesis of Compound 24 (Example)

Compound 24 was synthesized according to the following mechanism (Formula 10):

Formula 10

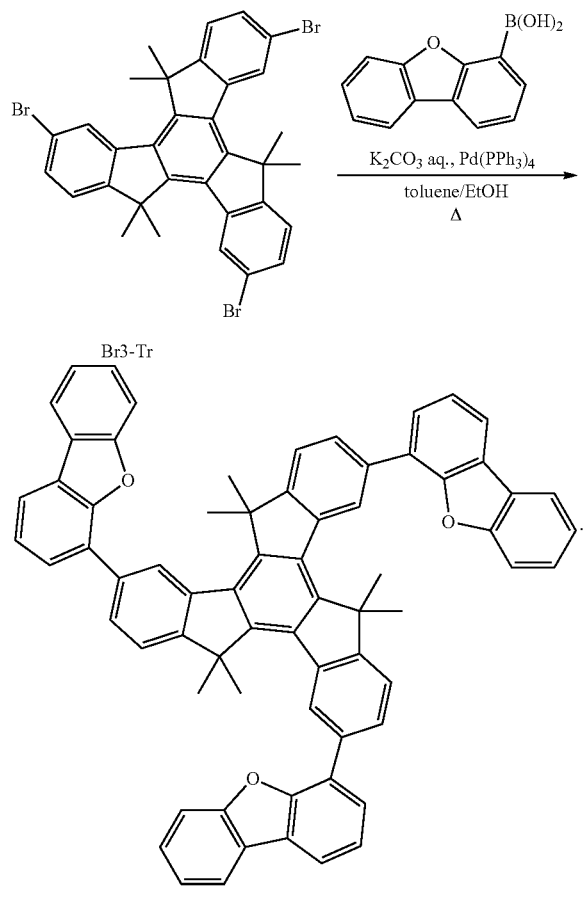

24

Br3-Tr (133 mg, 0.201 mmol), dibenzo[b,d]furan-4-ylboronic acid (191 mg, 0.901 mmol) and tetrakis(triphenylphosphine)palladium(0) (23.3 mg, 0.0202 mmol) were added to a mixture of toluene (7.1 mL) and ethanol (1.6 mL), and the reaction vessel was filled with nitrogen. Potassium carbonate (276 mg, 2.00 mol) dissolved in water (1.6 mL) was added thereto, and the mixture thus obtained was heated and stirred for about 14 hours at a temperature of 85° C. or less. The reaction mixture was allowed to cool to room temperature and concentrated under reduced pressure. The residue was extracted with chloroform and water using a separatory funnel, and the organic layer thus obtained was dried over magnesium sulfate and then filtered. The solvents were distilled under reduced pressure. The crude product thus obtained was separated by silica gel column chromatography (developing solvent: chloroform/hexane=1/2 by volume) and recrystallized from a mixture of ethyl acetate and ethanol to produce Compound 24 as a white solid (111 mg, 0.120 mmol, 60%).

$^1$H NMR (400 MHz, CDCl$_3$): δ 9.09 (s, 3H), 8.07 (d, J=7.7 Hz, 3H), 8.02 (dd, J=7.7 and 0.9 Hz, 3H), 7.87 (dd, J=7.3 and 0.9 Hz, 3H), 7.78 (d, J=7.2 Hz, 3H), 7.70 (d, J=8.2 Hz, 3H), 7.63 (d, J=8.2 Hz, 3H), 7.55-7.51 (m, 6H), 7.42 (t, J=7.7 Hz, 3H), 2.10 (s, 18H); $^{13}$C NMR (100 MHz, CDCl$_3$): δ 157.35, 156.39, 153.60, 149.08, 137.36, 135.90, 134.45, 127.46, 127.31, 126.97, 126.61, 126.56, 125.14, 124.52, 123.56, 122.98, 122.90, 120.95, 119.64, 111.87, 47.17, 24.31; MALDI-TOF MS (m/z): M$^+$ calc. for C$_{69}$H$_{48}$O$_3$, 924.36. found, 924.28.

Manufacture of Organic Electroluminescent Device

An organic electroluminescent device including a truxene derivative according to an embodiment of the present disclosure was manufactured using a coating method according to the following procedure:

Example 1

First, an ITO-glass substrate patterned and washed in advance was surface treated using ultraviolet (UV) rays/ozone (O$_3$). The thickness of the ITO layer (first electrode) on the glass substrate was about 150 nm.

Then, a mixture of water and isopropyl alcohol (1:1 v/v) was added to an undiluted solution of PEDOT:PSS (Heraeus Co. Ltd., trade name Clevios™, PVP CH8000) to prepare a solution for forming a hole injection layer. The solution for forming a hole injection layer was applied on the ITO-glass substrate by spin coating under processing conditions of about 2,000 rpm for about 2 seconds and then, about 4,000 rpm for about 60 seconds. The ITO-glass substrate coated with the solution was dried at about 105° C. for about 60 minutes to form a hole injection layer (thickness: about 40 nm) formed using PEDOT:PSS.

Then, 5 mg of Compound 1 as a truxene derivative, 0.50 mg of tris[2-(para-tolyppyridine]iridium(III) (Ir(mppy)$_3$), and 1.0 mg of 2-(4-tert-butylphenyl)-5-(4-biphenylyl)-1,3,4-oxydiazole (PBD) were dissolved in 0.35 mL of chloroform to obtain a solution for forming an emission layer. The solution for forming an emission layer was applied on the hole injection layer of the ITO-glass substrate by spin coating under processing conditions of about 2,000 rpm for about 10 seconds, and then about 3,000 rpm for about 20 seconds. Then, the ITO-glass substrate coated with the solution was dried at about 80° C. for about 30 minutes to form an emission layer (thickness: about 68 nm).

The substrate was transported to an evaporator for forming a metal layer, and an electron injection layer and a second electrode were deposited under a vacuum degree of about 3.0$^{-4}$ Pa to about 3.6$^{-4}$ Pa to manufacture an organic electroluminescent device. The electron injection layer was formed using CsF at a layer forming rate of about 0.1 Å/s to a layer thickness of about 1 nm, and the second electrode was formed using aluminum (Al) to a layer thickness of about 250 nm. The layer forming conditions during aluminum deposition included a layer forming rate of about 5.0 Å/s to a thickness of about 50 nm and then, a layer forming rate of about 11.0 Å/s to a thickness of about 200 nm.

Example 2

An organic electroluminescent device was manufactured using substantially the same procedure described in Example 1 except for using Compound 24 instead of Compound 1 as the truxene derivative.

Evaluation of Coating Layer and Layer Forming Properties

Examples 3 and 4 and Comparative Examples 1 and 2

Layer forming properties were evaluated for Compounds 1 and 22, 10,15-dihydro-5H-diindeno[1,2-a:1',2'-c]fluorene (truxene), and Ph3-Tr. The patterning and washing of ITO-glass substrates and the forming of hole injection layers (a layer of PEDOT:PSS) were performed as in Example 1. Then, 5 mg of Compound 1 or 22, truxene, or Ph3-Tr were dissolved in 0.3 mL of chloroform each to prepare truxene derivative solutions. The truxene derivative solutions were spin-coated on the hole injection layer of the ITO-glass substrate at about 2,000 rpm for about 10 seconds and about 3,000 rpm for about 20 seconds. Then, the ITO-glass substrate coated with the solution was dried at about 80° C. for about 30 minutes to form a truxene derivative layer.

The surface roughness and the layer thickness of each of the truxene derivative layers thus formed were measured. The surface roughness was obtained by measuring the surface of each truxene derivative layer over a range of 200 m×200 m using a nanoscale hybrid microscope VN-8010 (Keyence Co. Ltd.) equipped with a standard cantilever OP-75041, and computing the arithmetic mean (e.g., average) roughness (Ra) according to JIS B 0601-1994. For measuring the layer thickness, a cross-section was formed from the truxene derivative layer using a cutter, and height differences within each cross-section were measured and computed for a plurality of cross-sectional samples. The mean (e.g., average) value of the height difference was taken as the combined thickness of the hole injection layer and the truxene derivative layer, and the difference obtained by subtracting the thickness of the hole injection layer (about 40 nm) from the mean (e.g., average) value of the height difference was computed as the thickness of the truxene derivative. The results are shown in Table 1:

TABLE 1

| Corresponding Examples | Compound | Layer thickness (nm) | Surface roughness (nm) |
|---|---|---|---|
| Example 3 | Compound 1 | 61.0 | 1.1 |
| Example 4 | Compound 22 | 64.3 | 0.85 |
| Comparative Example 1 | Truxene | 85.5 | 39.8 |
| Comparative Example 2 | Ph3-Tr | 70.2 | 56.6 |

Referring to Table 1, the truxene derivatives of Compound 1 and 22 (used in Examples 3 and 4) formed truxene derivative layers having little (e.g., comparatively less) surface roughness and better layer forming properties compared to truxene and Ph3-Tr (were used in Comparative Examples 1 and 2). Accordingly, the emission layers of Examples 3 and 4 are considered to have more uniform layer thicknesses when compared to those of Comparative Examples 1 and 2, and performance limitations due to non-uniformity in each layer of a electroluminescent device (for example, short circuiting or uneven light emission due to non-uniformity in an applied electric field) may be prevented or reduced.

Evaluation of Device Characteristics

Performance evaluation results for the organic electroluminescent devices according to Example 4 and Comparative Example 1 are shown in Table 2. The emission properties of the organic electroluminescent devices thus manufactured were evaluated using a brightness light distribution characteristics measurement system of HAMAMATSU Photonics Co.

TABLE 2

| Example | Compound | Driving voltage (V) | External quantum extraction efficiency (%) |
|---|---|---|---|
| Example 1 | Compound 1 | 9.0 | 6.6 |
| Example 2 | Compound 24 | 11.5 | 5.0 |

Referring to the results in Table 2, the organic electroluminescent device including the truxene derivative according to an embodiment of the present disclosure illustrated comparatively good external quantum extraction efficiency.

According to the results, the truxene derivative according to an embodiment of the present disclosure has a structure represented by Formula 1 and has excellent layer forming properties. Performance limitations due to non-uniformity in each layer of a electroluminescent device including the truxene derivative according to an embodiment of the present disclosure (for example, short circuiting or uneven light emission due to non-uniformity in an applied electric field) are thought to be prevented or reduced.

As described above, according to the present disclosure, a truxene derivative having good layer forming properties, and an organic electroluminescent device including the truxene derivative are provided.

As used herein, expressions such as "at least one of", "one of", and "selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more example embodiments of the present disclosure have been described with reference to the accompanying drawings, it will be understood that the present disclosure should not be limited to these example embodiments, but that various changes and modifications can be made by one of ordinary skill in the art within the spirit and scope of the present disclosure as defined by the following claims and equivalents thereof.

What is claimed is:

1. An organic electroluminescent device, comprising:
a first electrode;
a hole transport layer and/or a hole injection layer;
an emission layer provided on the hole transport layer and/or hole injection layer; and
a second electrode provided on the emission layer,
wherein at least one of the hole transport layer, hole injection layer, or the emission layer comprises a truxene derivative represented by Formula 1:

Formula 1

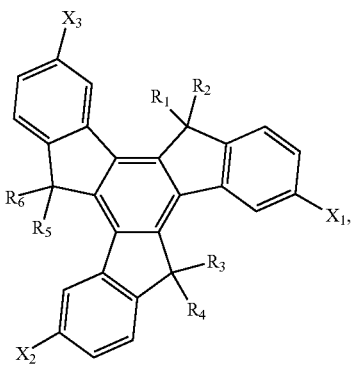

(1)

wherein $R_1$ to $R_6$ are each independently hydrogen, a substituted or unsubstituted linear, branched, or cyclic alkyl group having 1 to 16 carbon atoms, a substituted or unsubstituted linear or branched alkoxy group having 1 to 16 carbon atoms, a substituted or unsubstituted aryl group having 6 to 36 carbon atoms for forming a ring, or a substituted or unsubstituted heterocyclic group having 3 to 32 carbon atoms for forming a ring, and $X_1$, $X_2$, and $X_3$ are each independently a substituted or unsubstituted dibenzofuranyl group, a substituted or unsubstituted dibenzothienyl group, a substituted or unsubstituted carbazolyl group, or an unsubstituted 9,9-dimethyl-9H-fluorenyl group.

2. The organic electroluminescent device of claim 1, wherein $X_1$, $X_2$ and $X_3$ are the same group.

3. The organic electroluminescent device of claim 1, wherein $X_1$, $X_2$ and $X_3$ are each independently coupled with the truxene skeleton via a benzene ring position of the substituted or unsubstituted dibenzofuranyl group, the substituted or unsubstituted dibenzothienyl group, the substituted or unsubstituted carbazolyl group, or the unsubstituted 9,9-dimethyl-9H-fluorenyl group.

4. The organic electroluminescent device of claim 1, wherein $R_1$ to $R_6$ are each independently hydrogen, a substituted or unsubstituted linear, branched, or cyclic alkyl group having 1 to 7 carbon atoms, a substituted or unsubstituted linear or branched alkoxy group having 1 to 7 carbon atoms, or a substituted or unsubstituted aryl group having 6 to 12 carbon atoms for forming a ring.

5. The organic electroluminescent device of claim 1, wherein $R_1$ to $R_6$ are each independently a linear alkyl group having 1 to 7 carbon atoms, a phenyl group, or an alkylphenyl group.

6. The organic electroluminescent device of claim 1, wherein the truxene derivative is at least one of the compounds represented in Compound group 1:

Compound Group 1

1

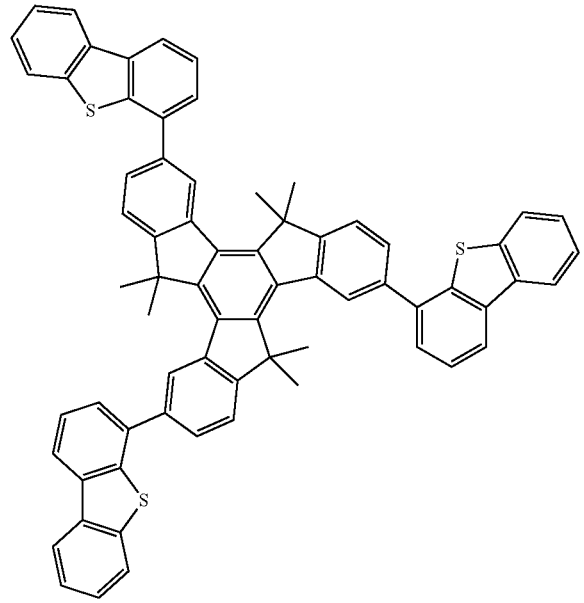

2

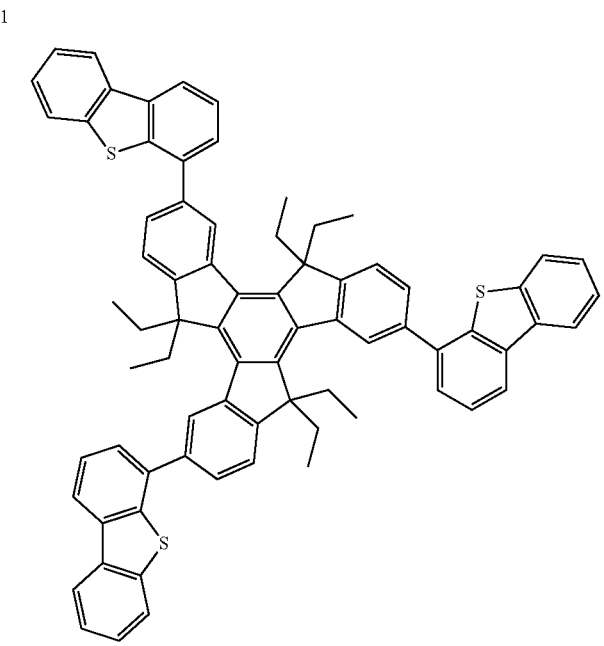

-continued
3
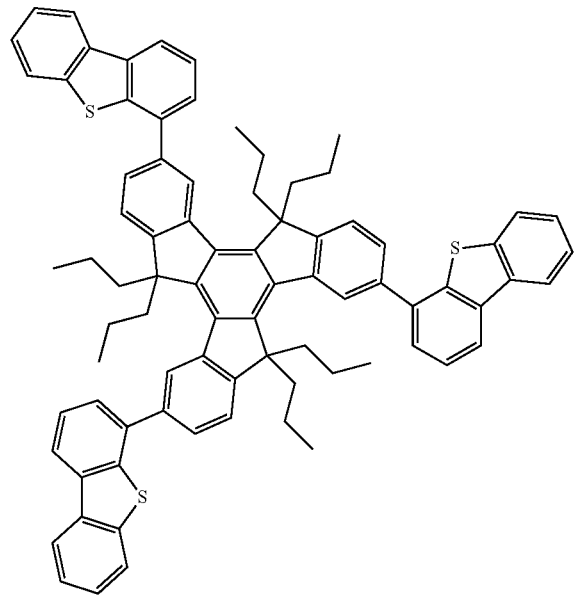
4
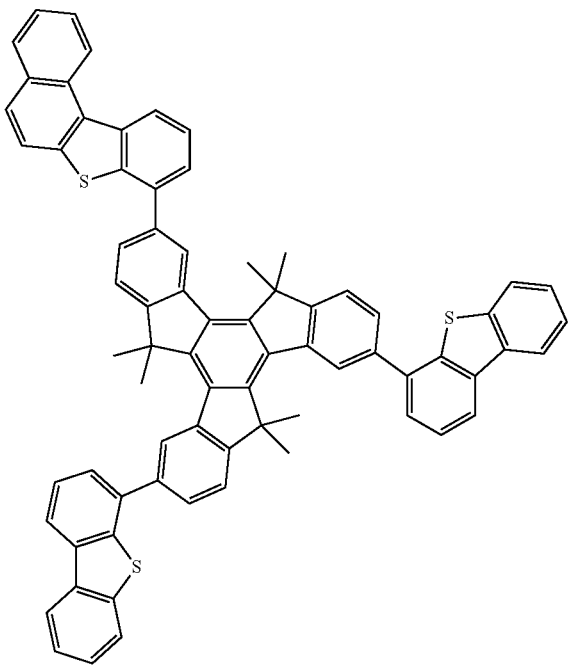
5
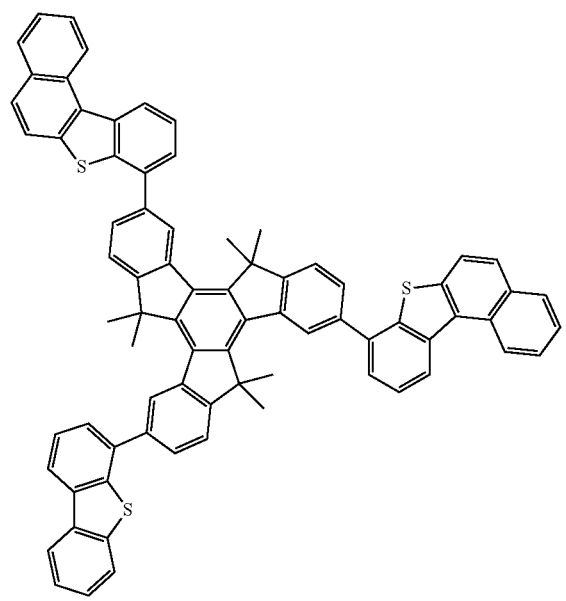
6
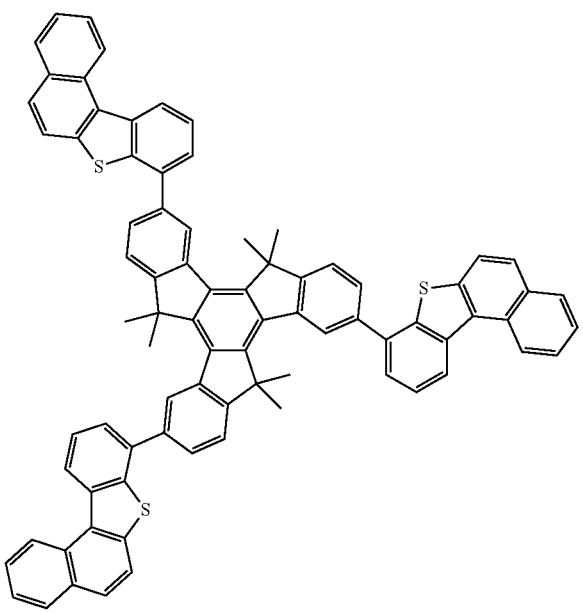

-continued
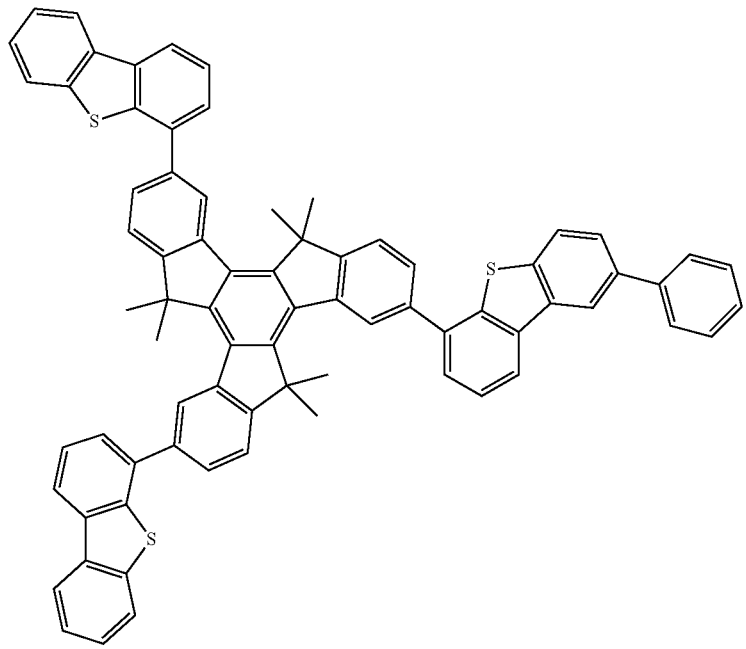
7
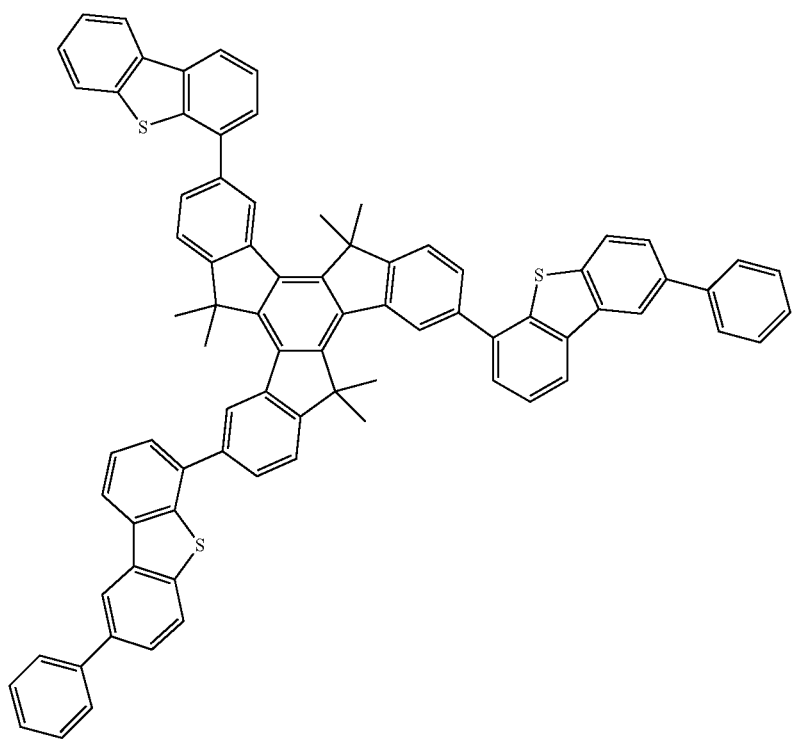
8

-continued
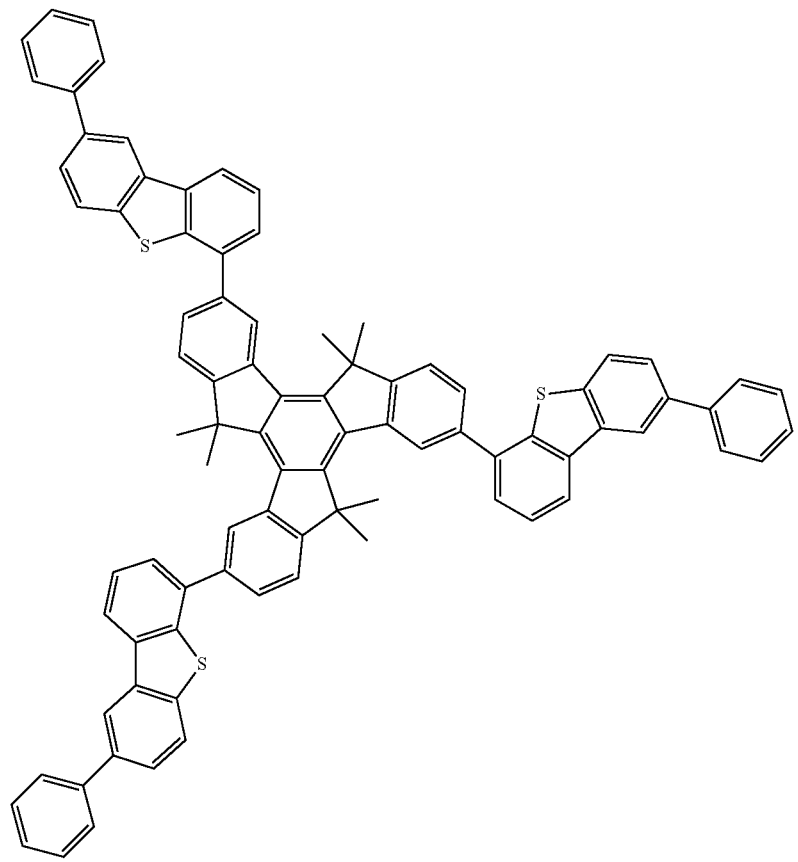
9
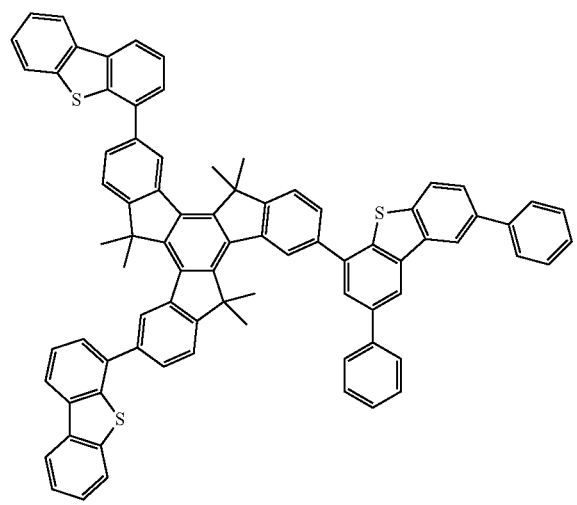
10
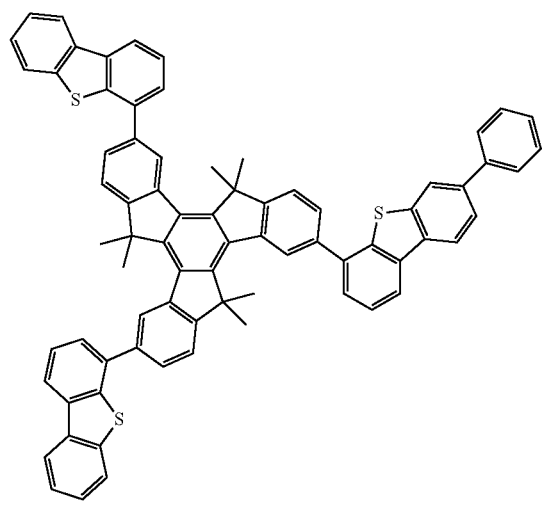
11

-continued
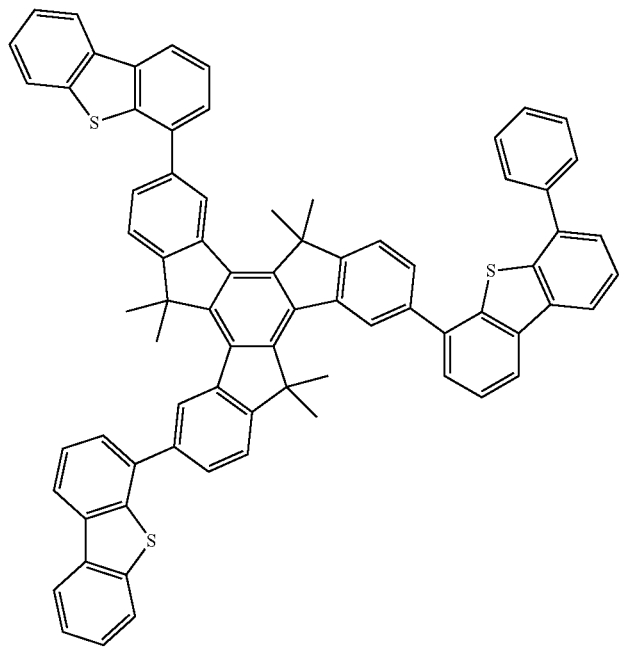
12
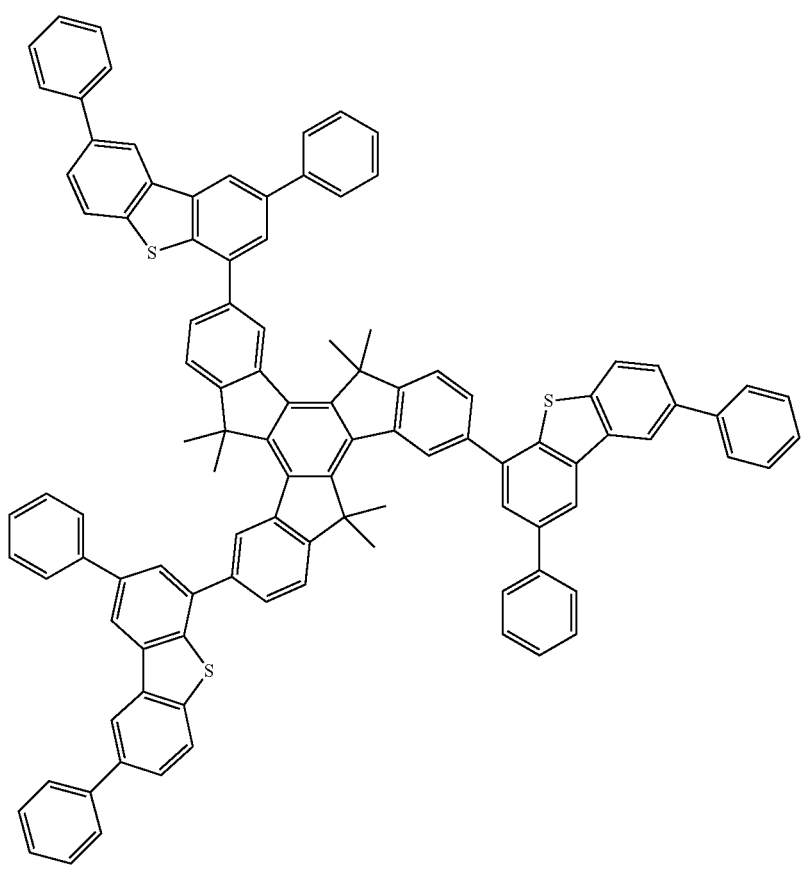
13

-continued
14
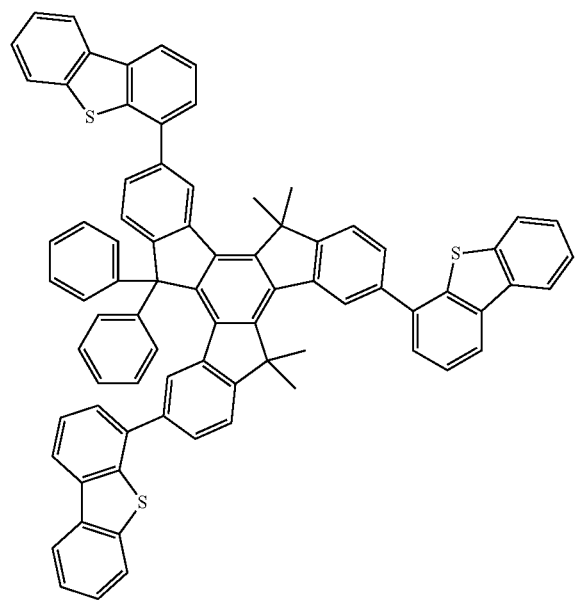
15
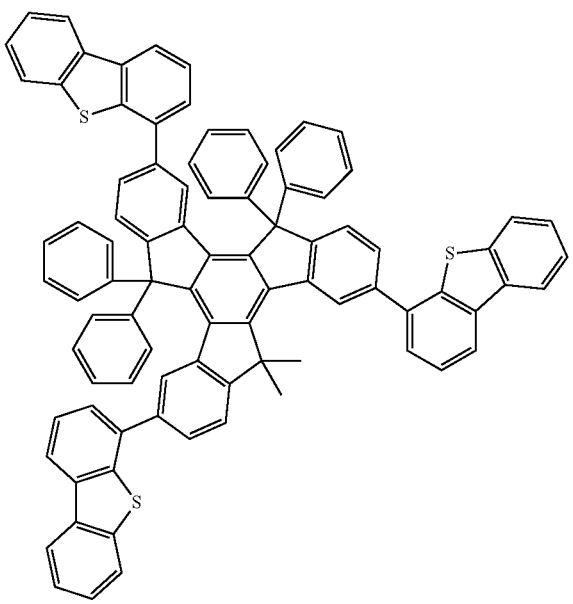
16
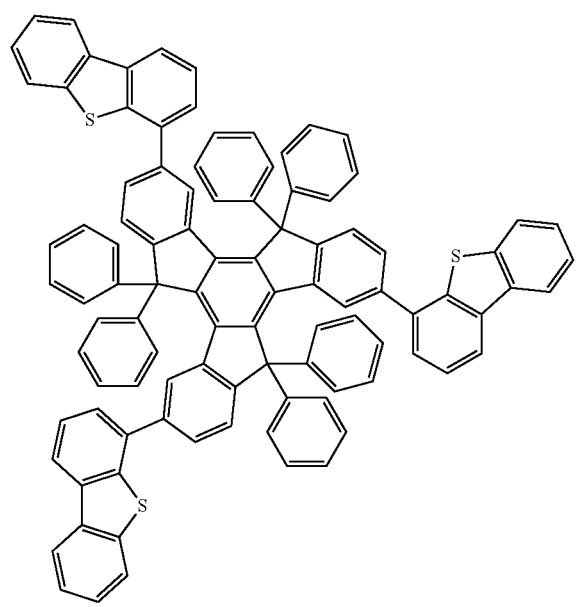
17
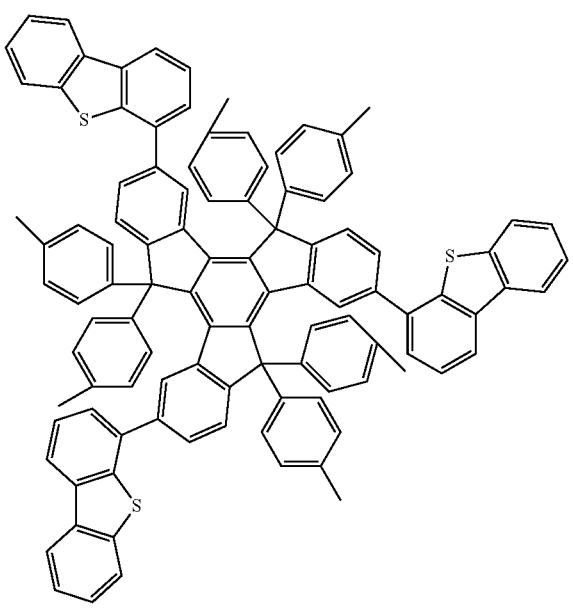

-continued
18
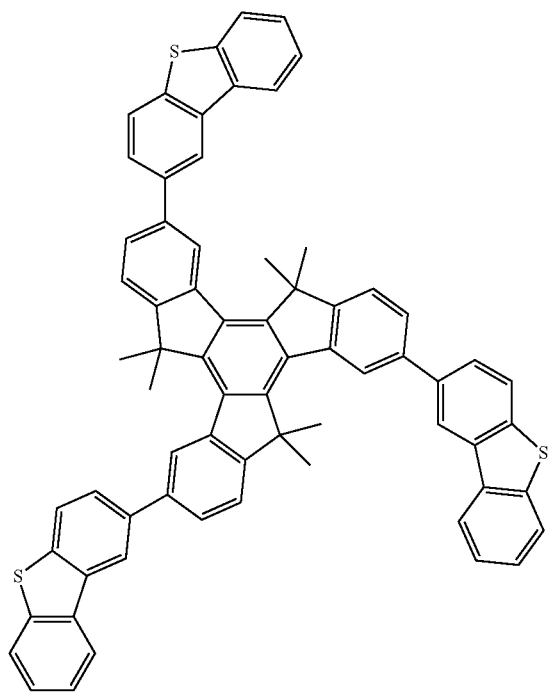
19
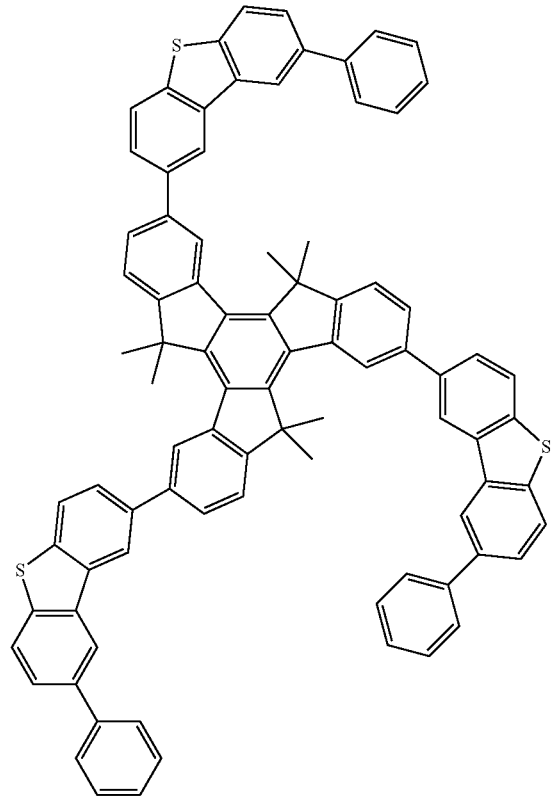
20
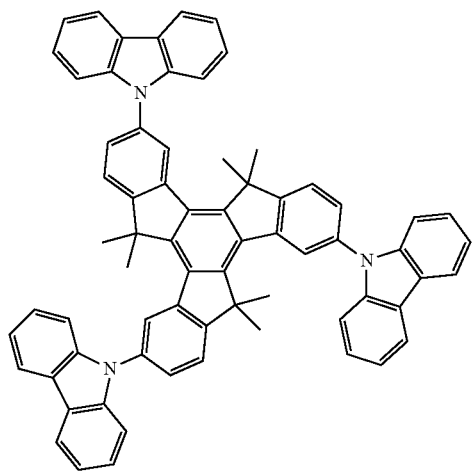
21
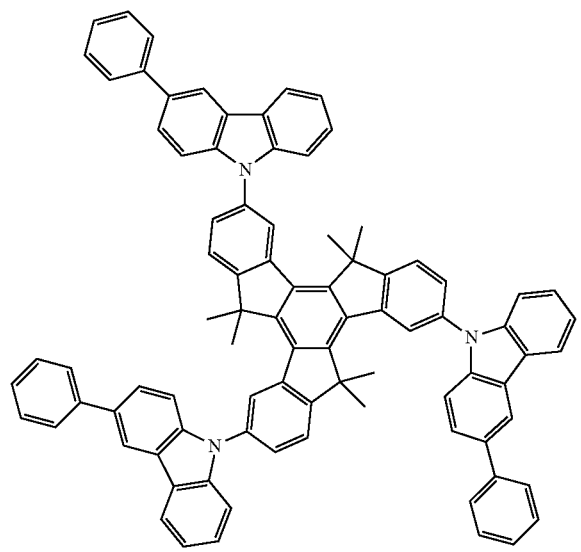

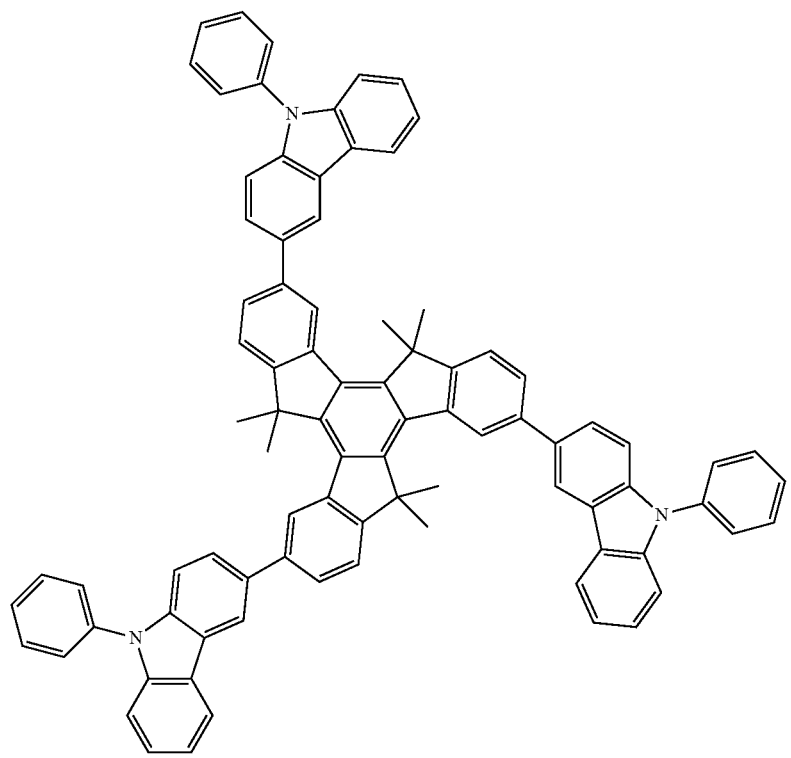
22
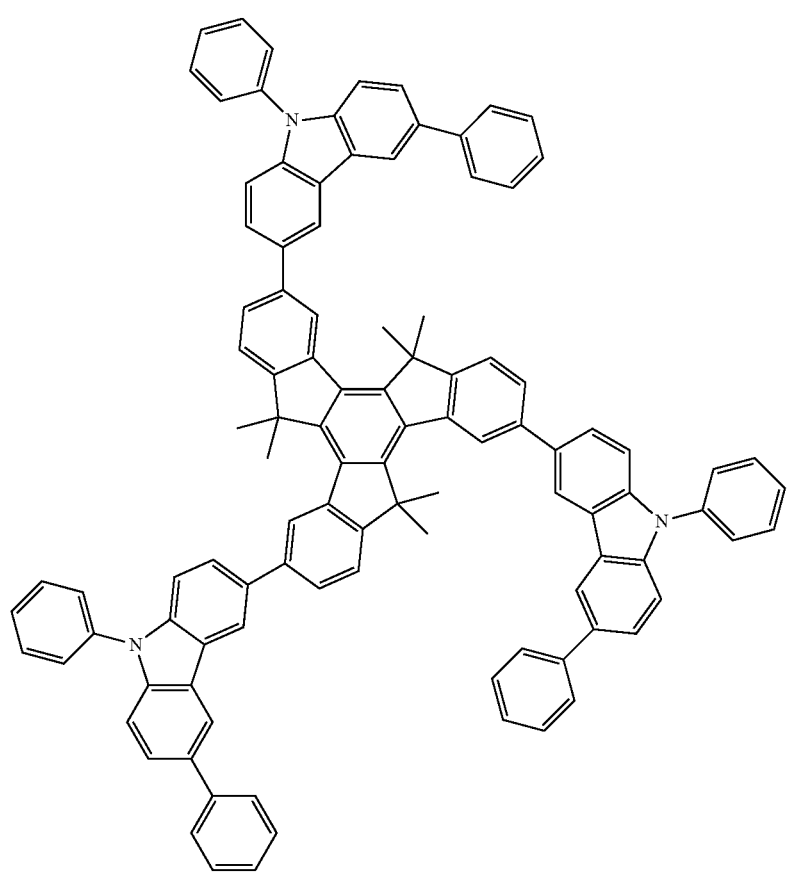
23

24
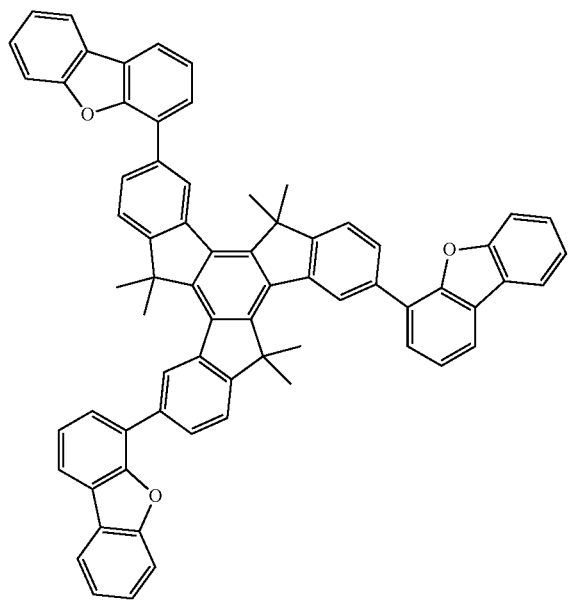
25
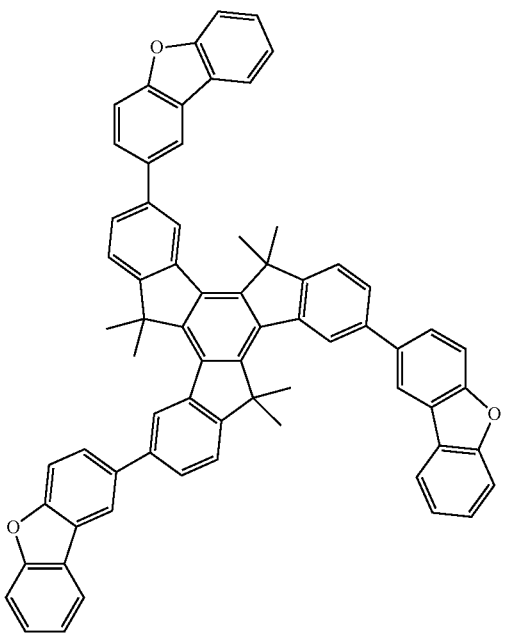
26
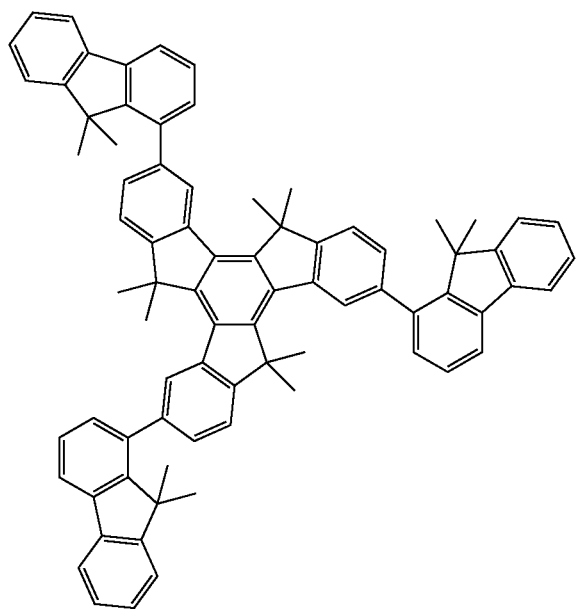
27
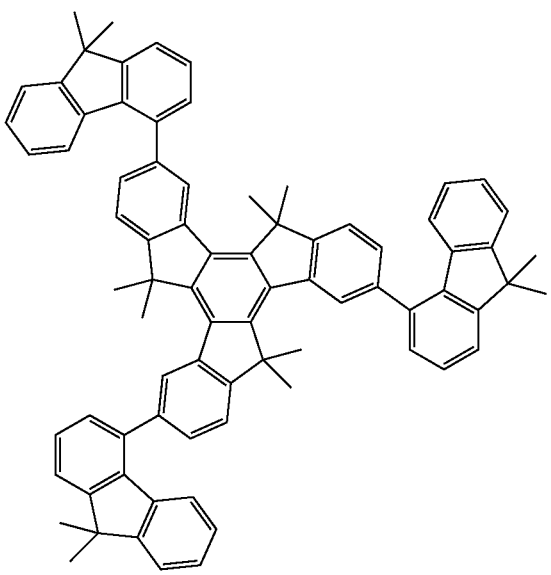

-continued

28
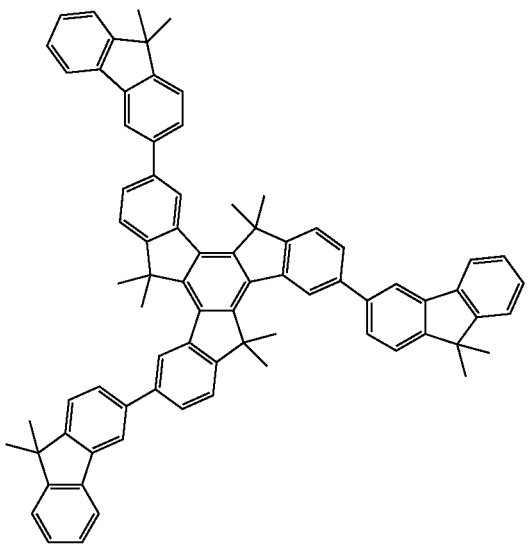

or

29
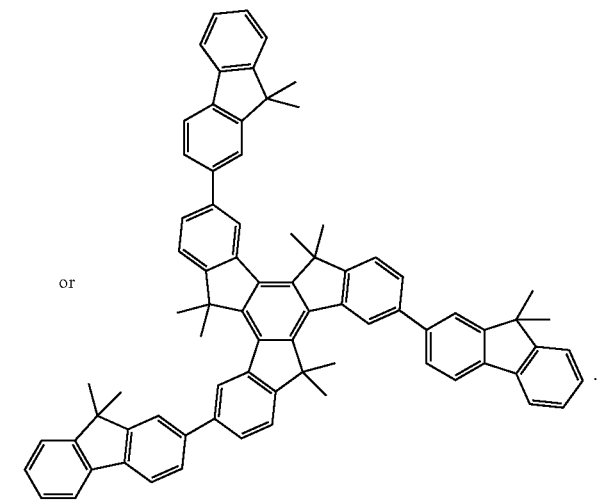

7. The organic electroluminescent device of claim 1, wherein the emission layer comprises the truxene derivative.

8. The organic electroluminescent device of claim 1, wherein the hole transport layer comprises the truxene derivative.

9. The organic electroluminescent device of claim 1, wherein the hole injection layer comprises the truxene derivative.

* * * * *